US008536316B2

(12) United States Patent
Soice et al.

(10) Patent No.: US 8,536,316 B2
(45) Date of Patent: Sep. 17, 2013

(54) METHODS FOR PURIFYING A TARGET PROTEIN FROM ONE OR MORE IMPURITIES IN A SAMPLE

(75) Inventors: Neil Soice, Amherst, NH (US); John Dana Hubbard, Billerica, MA (US); Yu Zhang, Chelmsford, MA (US); James Hamzik, Waltham, MA (US)

(73) Assignee: EMD Millipore Corporation, Billerica, MA (US)

( * ) Notice: Subject to any disclaimer, the term of this patent is extended or adjusted under 35 U.S.C. 154(b) by 375 days.

(21) Appl. No.: 12/851,082

(22) Filed: Aug. 5, 2010

(65) Prior Publication Data

US 2011/0065901 A1    Mar. 17, 2011

Related U.S. Application Data

(60) Provisional application No. 61/273,709, filed on Aug. 7, 2009.

(51) Int. Cl.
*A23J 1/00* (2006.01)
*C07K 1/00* (2006.01)

(52) U.S. Cl.
USPC .......................................... 530/413; 530/416

(58) Field of Classification Search
None
See application file for complete search history.

(56) References Cited

U.S. PATENT DOCUMENTS

| | | | |
|---|---|---|---|
| 4,490,937 | A | 1/1985 | Yavnieli |
| 4,816,567 | A | 3/1989 | Cabilly et al. |
| 5,091,178 | A | 2/1992 | Hellstrom et al. |
| 5,256,694 | A | 10/1993 | Wuest et al. |
| 6,054,051 | A | 4/2000 | van Reis |
| 7,323,553 | B2 | 1/2008 | Fahrner et al. |
| 8,168,185 | B2 * | 5/2012 | Eon-Duval et al. ........ 424/133.1 |
| 2006/0142549 | A1 * | 6/2006 | Takeda et al. ................. 530/351 |
| 2006/0194953 | A1 | 8/2006 | Bonnerjea et al. |
| 2008/0312425 | A1 * | 12/2008 | Bonnerjea et al. ............ 530/413 |
| 2009/0050566 | A1 | 2/2009 | Kozlov et al. |
| 2009/0149638 | A1 | 6/2009 | Ley et al. |
| 2011/0105725 | A1 | 5/2011 | Nielsen et al. |

FOREIGN PATENT DOCUMENTS

| | | | |
|---|---|---|---|
| WO | 2009/138484 A2 | 11/2009 | |
| WO | WO 2009138484 A2 * | 11/2009 | |
| WO | WO 2010048192 A2 * | 4/2010 | |

OTHER PUBLICATIONS

Pete Gagnon, "Polishing Methods for Monoclonal IgG Purification" Chapter 17 from "Process Scale Bioseparations for teh Biopharmaceutical Industry", 2006, CRC Press, pp. 491-506.*
"Buffers: A guide for the preparation and use of buffers in biological systems", Edited by Gueffroy, Donald E., Calbiochem Brand Biochemicals, Copyright 1975 by Behring Diagnostics, pp. 1-24.
Berg et al., "Bispecific Antibodies that Mediate Killing of Cells Infected with Human Immunodeficiency Virus of any Strain", Proceedings of the National Academy of Sciences, vol. 88, Jun. 1991, pp. 4723-4727.
Chamow et al., "A Humanized, Bispecific Immunoadhesin-Antibody That Retargets CD3+ Effectors to Kill HIV-1-Infected Cells", The Journal of Immunology, vol. 153, No. 9, Nov. 1, 1994, pp. 4268-4280.
Chothia et al., "Canonical Structures for the Hypervariable Regions of Immunoglobulins", Journal of Molecular Biology, vol. 196, No. 4, Aug. 20, 1987, pp. 901-917.
Clackson et al., "Making antibody fragments using phage display libraries", Nature, vol. 352, Aug. 15, 1991, pp. 624-628.
Giovannoni et al., "Antibody Purification Using Membrane Adsorbers", BioPharm International, Dec. 1, 2008, 6 pages.
Hamzik et al., "Chromatographic Three Step Antibody Purification Process with No Intermediate Tanks", Millipore Corporation, May 2010, 1 page.
International Search Report received for PCT Patent Application No. PCT/US2010/044539, mailed on Oct. 14, 2010, 2 pages.
Jones et al., "Replacing the complementarity-determining regions in a human antibody with those from a mouse", Nature, vol. 321, May 29, 1986, pp. 522-525.
Kellogg et al., "Purification of a Multiprotein Complex Containing Centrosomal Proteins from the Drosophila Embryo by Chromatography With Low-Affinity Polyclonal Antibodies", Molecular Biology of the Cell, vol. 3, Jan. 1992, pp. 1-11.
Kohler et al., "Continuous cultures of fused cells secreting antibody of predefined specificity", Nature, vol. 256 (Attached version of the document is reprinted with permission in The Journal of Immunology, 2005, vol. 174, pp. 2453-2455), Aug. 7, 1975, pp. 495-497.
Lindmark et al., "Binding of Immunoglobulins to Protein A and Immunoglobulin Levels in Mammalian Sera", Journal of Immunological Methods, vol. 62, No. 1, 1983, pp. 1-13.
Marks et al., "By-passing Immunization: Human Antibodies from V-gene Libraries Displayed on Phage", Journal of Molecular Biology, vol. 222, No. 3, Dec. 5. 1991, pp. 581-597.
Morrison et al., "Chimeric human antibody molecules: Mouse antigen-binding domains with human constant region domains", Proceedings of the National Academy of Sciences, vol. 81, Nov. 1984, pp. 6851-6855.
Presta, Leonard G., "Antibody engineering", Current Opinion in Structural Biology, vol. 2, No. 4, Aug. 1992, pp. 593-596.
Riechmann et al., "Reshaping human antibodies for therapy", Nature, vol. 332, Mar. 24, 1988, pp. 323-327.
Zeman et al., "Microfiltration and Ultrafiltration: Principles and Applications", Marcel Dekker, Inc., 1996, pp. 299-301.
Disclosed Anonymously, "Low pH virus inactivation performed on a chromatography column", IP.com Prior Art Database Disclosure, Disclosure No. IPCOM000183319D dated May 18, 2009, Originally published in Prior Art Database, pp. 1.

* cited by examiner

*Primary Examiner* — Daniel E Kolker
*Assistant Examiner* — James Rogers
(74) *Attorney, Agent, or Firm* — EMD Millipore Corporation

(57) ABSTRACT

The present invention relates, at least in part, to improved methods of protein purification. In particular, the present invention relates, at least in part, to methods for purifying an Fc region containing protein from a composition comprising the Fc region containing protein and one or more impurities, where the methods eliminate the need for a holding tank and/or a buffer exchange step.

16 Claims, 7 Drawing Sheets

METHODS FOR PURIFYING A TARGET PROTEIN FROM ONE OR MORE IMPURITIES IN A SAMPLE

RELATED APPLICATIONS

The present application claims the benefit of priority of U.S. Provisional Patent Application No. 61/273,709, filing date Aug. 7, 2009, the entire contents of which are incorporated herein in their entirety.

FIELD OF THE INVENTION

The present invention relates, at least in part, to methods of protein purification. In particular, the present invention relates, at least in part, to methods for purifying a target protein (e.g., Fc region containing proteins such as, e.g., antibodies and fragments thereof and antibody-like molecules such as, e.g., immunoadhesins) from a composition comprising the target protein and one or more impurities.

BACKGROUND

Efficient and economic large scale purification of proteins, e.g., therapeutic proteins including antibodies, is an increasingly important consideration for the biotechnology and pharmaceutical industries. Generally, the processes for protein purification are quite elaborate and expensive and include many different steps. For example, typically, proteins are produced using cell culture methods, e.g., using either mammalian or bacterial cell lines engineered to produce the protein of interest by insertion of a recombinant plasmid containing the gene for that protein. In general, separation of the desired protein from the media components which are fed to the cells and from the by-products of the cells themselves as well as any other impurities that may exist poses a formidable challenge. Such separation is especially important when the therapeutic proteins are meant for use in humans and have to be approved by the Food and Drug Administration.

In general, the purification processes that are currently being used, include at least the following steps: cell lysis to recover an intracellular protein or recovery of a protein from the media in case of a secreted protein; removal of cellular debris using differential centrifugation or filtration to obtain a clarified sample containing the protein of interest; use of a variety of chromatography media in a multi-step process to separate a protein of interest from the various impurities in the sample.

Commonly used chromatography methods include one or more of affinity chromatography media, ion exchange chromatography media, hydrophobic interaction, hydrophilic interaction, size exclusion and mixed mode (i.e., combination of various chromatography methods). For example, for purification of monoclonal antibodies, several processes have been described, most of which include an initial Protein A affinity capture step followed by one or more ion exchange polishing steps. Further, other chromatography technologies, such as: bind and elute hydrophobic interaction chromatography (HIC); flow-through hydrophobic interaction chromatography (FTHIC); mixed mode chromatography techniques, e.g., bind and elute weak cation and anion exchange (Abx), bind and elute hydrophobic and ion exchange interaction and flow-through hydrophobic and ion exchange mixed mode interaction (FTMM), both of which can utilize resins such as Capto Adhere, Capto MMC, HEA Hypercel, PPA Hypercel, may be used. Additionally, hydrophobic charge induction (HCI) chromatography along with others and combinations of various techniques can be used for polishing. Generally, it is important for the polishing steps to contain an anion exchange step to provide an additional, orthogonal virus removal step.

Although, protein purification methods involving a combination of various chromatography steps have been described, as discussed above, these methods require the use of a holding tank and/or a buffer exchange step between each chromatography step. Typically, the target protein is eluted into a holding tank where the buffer/solution conditions are adjusted such that they are suitable for the next chromatography step (referred to as buffer exchange). The conditions of the buffer in the holding tank, e.g., pH., salt etc., are typically adjusted as necessary, prior to loading onto to the next chromatography media or a filtration membrane.

SUMMARY OF THE INVENTION

The present invention provides, at least in part, improved methods of purifying or separating a protein of interest from one or more impurities, where the methods eliminate the need for a holding tank and/or a buffer exchange step between various chromatography steps.

In various embodiments, the present invention provides for the purification of Fc region containing proteins (e.g., monoclonal antibodies and similar proteins) with a robust template, however, avoids intermediate holding tank or buffer exchange steps. Accordingly, the purification process may be referred to as a "connected process." The process encompasses the use of appropriate conditions and chromatography media to achieve a continuous, holding tank free process.

In some embodiments according to the invention, a method for purifying an Fc region containing target protein from one or more impurities in a sample is provided, where the method comprises the steps of: (a) contacting the sample with an affinity chromatography media; (b) eluting the Fc region containing target protein from the affinity media; (c) contacting the eluate with a cation exchange chromatography media; (d) eluting the Fc region containing target protein from the cation exchange chromatography media; (e) contacting the eluate with an anion exchange chromatography media; and (f) recovering the Fc region containing target protein, where the method eliminates the need for a holding tank between steps (b) and (c) and steps (d) and (e).

In other embodiments according to the invention, a method for purifying an Fc region containing target protein from one or more impurities in a sample is provided, where the method comprises the steps of: (a) contacting the sample with an affinity chromatography media; (b) eluting the Fc region containing target protein from the affinity media; (c) contacting the eluate with a cation exchange chromatography media; (d) eluting the Fc region containing target protein from the cation exchange chromatography media; (e) contacting the eluate with an anion exchange chromatography media; and (f) recovering the Fc region containing target protein, where the method eliminates the need for a buffer exchange step between steps (b) and (c) and steps (d) and (e).

In still other embodiments according to the invention, a method for purifying an Fc region containing target protein from one or more impurities in a sample is provided, where the method comprises the steps of: (a) contacting the sample with an affinity chromatography media; (b) eluting the Fc region containing target protein from the affinity media; (c) contacting the eluate with a cation exchange chromatography media; (d) eluting the Fc region containing target protein from the cation exchange chromatography media; (e) contacting the eluate with an anion exchange chromatography media; and (f) recovering the Fc region containing target protein, where the method eliminates the need for a holding tank and a buffer exchange step between steps (b) and (c) and steps (d) and (e).

In some embodiments according to the methods of the claimed invention, the methods further comprise a pre-elution step between steps (a) and (b). In various embodiments, the pre-elution step comprises contacting the affinity chromatography media of step (a) with a cation exchange chromatography buffer.

In various embodiments, the claimed methods are useful for purifying an Fc region containing target protein from one or more impurities. Such an Fc region containing target proteins include, but are not limited to, an antibody, an immunoadhesion molecule and an Fc fusion protein, and Fc containing fragments thereof. In a particular embodiment, an Fc region containing target protein is a monoclonal antibody.

In various embodiments, the Fc region containing target protein is eluted from the affinity media using a buffer having a pH ranging from 2.0 to 4.0.

In some embodiments, step (d) comprises the use of a buffer having a pH ranging from 5.0 to 9.0. In yet other embodiments, step (d) comprises use of a buffer having a pH ranging from 6.0 to 8.0.

In some embodiments, the affinity chromatography media step in the methods of the invention comprises use of Protein A or a functional variant thereof.

In some embodiments, the methods according to the invention further include a virus inactivation step between the steps (c) and (d). In some embodiments, the virus inactivation step comprises contacting the cation exchange chromatography media with a buffer having a pH lower than 4.0 for a period of time suitable for viral inactivation. The period of time usually ranges from 15 through 60 minutes.

Also provided herein are kits for purifying an Fc region containing target protein from one or more impurities in a sample. In some embodiments, such a kit comprises one or more of: an affinity chromatography column, a cation exchange chromatography column, an anion exchange chromatography column and one or more elution buffers along with instructions for using the kit.

In some embodiments, the one or more chromatography columns included in the kit are disposable.

DETAILED DESCRIPTION OF THE INVENTION

Figure 1:
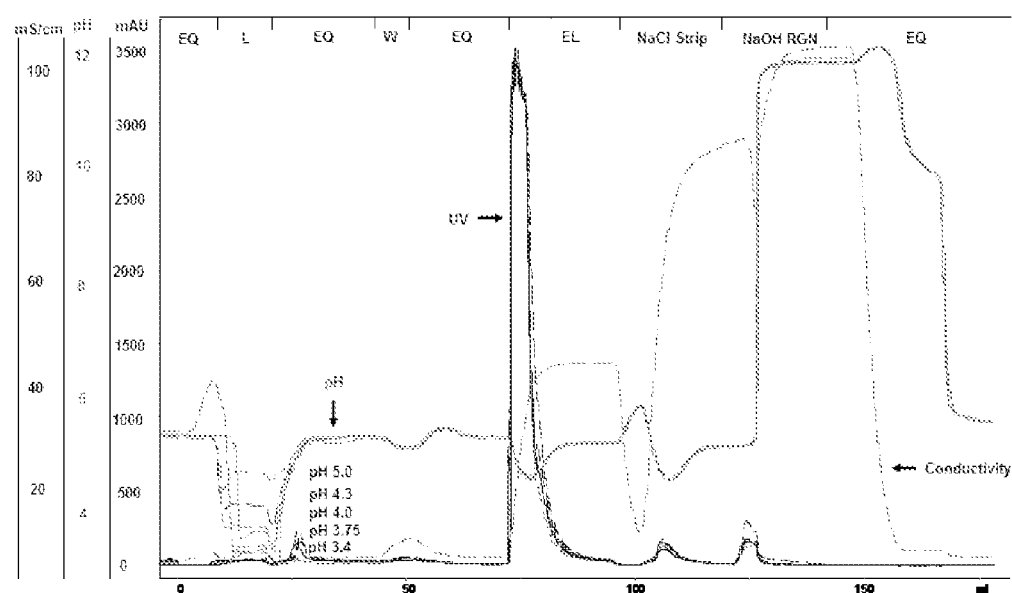
FIG. 1 depicts chromatograms for loading samples under various pH conditions onto a cation exchange column.

The present invention provides, at least in part, novel and improved methods for purifying a target protein from a sample containing the target protein and one or more impurities, where the methods specifically eliminate the need for a holding tank and/or a buffer exchange step, one or both of which are typically performed between various chromatography steps which form part of a conventional protein purification process.

The methods described herein are inventive and more efficient over those described in the art, in that, they reduce process restrictions and provide a template for a disposable or partially disposable process, where liquid handling can be challenging. The process could be applied to any Protein A binding polypeptide (e.g., containing an Fc region), such as monoclonal antibodies and fragments containing Fc region, immunoadhesion molecules and Fc fusion proteins. In some embodiments, the process conditions depend on the pI value for the target molecule being purified, which can be readily determined by one of ordinary skill in the art. The buffers described herein work best for Fc region containing proteins such as monoclonal antibodies having a pI greater than 8.0. However, the process can be readily optimized for proteins having a pI lower than 8.0, based on the teachings of the art and those described herein.

I. Definitions

In order that the present disclosure may be more readily understood, certain terms are first defined. Additional definitions are set forth throughout the detailed description.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. Immunoglobulins or antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991).

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5$^{th}$ Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody may comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In a particular embodiment, a nucleic acid molecule comprises a nucleotide sequence encoding a variant of SpA.

As used herein, the term "immunoadhesin" designates antibody-like molecules which combine the "binding domain" of a heterologous "adhesion" protein (e.g., a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e., is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by Protein A chromatography (Lindmark et al., J. Immunol. Meth. 62:1-13 (1983)).

An "antibody-immunoadhesin chimera" comprises a molecule which combines at least one domain of an antibody (e.g., an Fc region) with at least one immunoadhesin molecule. Exemplary antibody-immunoadhesin chimeras are the bispecific CD4-IgG chimeras described in Berg et al., PNAS (USA) 88:4723-4727 (1991) and Chamow et al., J. Immunol. 153:4268 (1994).

The term "Fc region" and "Fc region containing protein" means that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as $CH_2$/$CH_3$ regions, can bind selectively to affinity ligands such as Protein A or functional variants thereof. In some embodiments, an Fc region containing protein specifically binds Protein A or a functional derivative, variant or fragment thereof. In other embodiments, an Fc region containing protein specifically binds Protein G or Protein L, or functional derivatives, variants or fragments thereof.

The term "ligand binding domain" as used herein refers to any native cell-surface receptor or any region or derivative thereof retaining at least a qualitative ligand binding of a corresponding native receptor. In some embodiments according to the claimed invention, a ligand binding domain is fused to an Fc region. In a specific embodiment, the receptor for the ligand is derived from a cell-surface polypeptide having an extracellular domain which is homologous to a member of the immunoglobulin super gene family. In general, any receptor may be used in the methods of the invention, so long as it includes or is fused to an Fc region, as defined herein. Other receptors, which are not members of the immunoglobulin super gene family but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-selectins).

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors. In some embodiments, a receptor binding domain contains or is fused to an Fc region, as described herein.

The term "composition", "solution" or "sample" to be purified herein comprises the target protein (e.g., an Fc region containing protein) and one or more impurities. The composition or sample may be "partially purified" (i.e., having been subjected to one or more purification steps, such as by non-affinity chromatography described herein) or may be obtained directly from a host cell or organism producing the polypeptide (e.g., the composition may comprise harvested cell culture fluid).

As used herein, the term "polypeptide" refers generally to peptides and proteins having more than about ten amino acids. The terms "protein of interest" and "target protein," as used interchangeably herein, refer to a protein or polypeptide, including but not limited to, an Fc region containing protein such as an antibody that is to be purified by a method of the invention, from a mixture of proteins and, optionally, other materials such as cell debris and the like.

As discussed above, in some embodiments, a target protein is an Fc region containing protein, e.g., an immunoglobulin. In some embodiments, an Fc region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 CD20, CD34, and CD40; erythropoietin; osteoinductive factors; immunotoxins; a bone morphogenetic protein (BMP); an interferon such as interferon-α, -β, and γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides. In addition, a protein or polypeptide of the invention is an antibody, fragment or variant thereof, that binds specifically to any of the above-listed polypeptides.

The term "acidic variant" is a variant of a target protein which is more acidic (e.g. as determined by cation exchange chromatography) than the target protein. An example of an acidic variant is a deamidated variant.

The terms "contaminant," "impurity," and "debris," as used interchangeably herein, refer to any foreign or objectionable molecule, including a biological macromolecule such as a DNA, an RNA, one or more host cell proteins, endotoxins, lipids and one or more additives which may be present in a sample containing the Fc containing target protein that is being separated from one or more of the foreign or objectionable molecules using a process of the present invention. Additionally, such a contaminant may include any reagent which is used in a step which may occur prior to the purification process.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid ("HCCF")) comprising a protein of interest such as an antibody or immunoadhesin expressed in a CHO cell). The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture. It is understood that where the host cell is another cell type, e.g., a mammalian cell besides CHO, an *E. coli*, a yeast, an insect cell, or a plant cell, HCP refers to the proteins, other than target protein, found in a lysate of the host cell.

The term "parts per million" or "ppm" are used interchangeably herein to refer to a measure of purity of a target protein purified by a method of the invention. The units ppm refer to the amount of HCP or CHOP in nanograms/milliliter per protein of interest in milligrams/milliliter (i.e., CHOP ppm=(CHOP ng/ml)/(protein of interest mg/ml), where the proteins are in solution). Where the proteins are dried (such as by lyophilization), ppm refers to (CHOP ng)/(protein of interest mg)).

The terms "purifying," "separating," or "isolating," as used interchangeably herein, refer to increasing the degree of purity of a polypeptide or protein of interest or a target protein from a composition or sample comprising the polypeptide and one or more impurities. Typically, the degree of purity of the target protein is increased by removing (completely or partially) at least one impurity from the composition. A "purification step" may be part of an overall purification process resulting in a "homogeneous" composition or sample, which is used herein to refer to a composition or sample comprising less than 100 ppm HCP in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm of HCP.

The terms "flow-through process," "flow-through mode," and "flow-through chromatography," as used interchangeably herein, refer to a product separation technique in which at least one product (e.g., an Fc region containing protein) contained in a sample along with one or more contaminants is intended to flow through a chromatographic resin or media, while at least one potential contaminant or impurity binds to the chromatographic resin or media. The "flow-through mode" is generally an isocratic operation (i.e., a chromatography process during which the composition of the mobile phase is not changed).

In some embodiments according to the claimed methods and as described in the Examples set forth herein, the methods employ an anion exchange chromatography step which is performed in a flow-through mode.

The terms "bind and elute mode" and "bind and elute process," as used interchangeably herein, refer to a product separation technique in which at least one product contained in a sample (e.g., an Fc region containing protein) binds to a chromatographic resin or media and is subsequently eluted.

As used herein, the terms "holding tank," "pool tank," and "intermediate tank," as used interchangeably herein, refer to any container, tank or bag, which may be used to collect the output of a process step (e.g., an eluate from a column). In most conventional processes, one or more intermediate containers are used for adjusting the conditions/properties of the output from one process step to make it suitable for the next process step. For example, it may be necessary to adjust the pH and/or conductivity of an eluate from a chromatography column or step (e.g., containing protein target and impurities) before loading the pool onto the next chromatography column or step. In various embodiments according to the methods of the present invention, the need for a holding tank is obviated. Accordingly, in various embodiments of the claimed methods, the methods provide an improved way to purify a target protein from one or more impurities without the need for a holding tank, which is typically used in conventional purification processes.

As used herein, the term "connected process" refers to a purification process for an Fc region containing protein, which obviates the need for a holding tank and/or a buffer exchange step. Accordingly, the connected processes according to the claimed invention are superior to the conventional purification processes currently used in the art, as they provide significant savings of both time as well as resources.

As used herein, the term "buffer exchange step" refers to an in-line solution condition adjustment, which is typically an alternative in many conventional processes, to the use of a holding tank, as described above. In a typical buffer exchange step, two solutions can be mixed or titrated during transfer using solution blending in a pipe or mixing vessel, filtration device or apparatus. For example, a solution may be required to be diluted in order to reduce conductivity by blending the solution with another lower conductivity solution. Buffer exchange can be accomplished with the help of filtration devices, such as diafiltration, ultrafiltration and the like. In some embodiments according to the claimed invention, the methods provide an improved process for purifying proteins, which eliminates the need for a buffer exchange step.

In some other embodiments, methods according to the claimed invention obviate the need for both a holding tank as well as a buffer exchange step.

The term "chromatography" refers to any kind of technique which separates an analyte of interest (e.g., an Fc region containing protein such as an immunoglobulin) from other molecules present in a mixture. Usually, the analyte of interest is separated from other molecules as a result of differences in rates at which the individual molecules of the mixture migrate through a stationary medium under the influence of a moving phase, or in bind and elute processes.

The term "chromatography resin" or "chromatography media" are used interchangeably herein and refer to any kind of solid phase which separates an analyte of interest (e.g., an Fc region containing protein such as an immunoglobulin) from other molecules present in a mixture. Usually, the analyte of interest is separated from other molecules as a result of differences in rates at which the individual molecules of the mixture migrate through a stationary solid phase under the influence of a moving phase, or in bind and elute processes. Non-limiting examples include cation exchange resins, affinity resins, anion exchange resins, anion exchange membranes, hydrophobic interaction resins and ion exchange monoliths.

The term "affinity separation," or "affinity purification," as used herein, refers to any purification or assaying technique which involves the contacting a sample containing a target analyte (e.g., an Fc region containing protein such as an immunoglobulin) with an affinity media (e.g., a solid support carrying on it an affinity ligand known to bind the analyte such as, for example, e.g., Protein A or a variant thereof) known to bind the target analyte.

The terms "affinity chromatography" and "protein affinity chromatography," as used interchangeably herein, refer to a protein separation technique in which a target protein (e.g., an Fc region containing protein of interest or antibody) is specifically bound to a ligand which is specific for the target protein. Such a ligand is generally referred to as a biospecific ligand. In some embodiments, the biospecific ligand (e.g., Protein A or a functional variant thereof) is covalently attached to a chromatographic solid phase material and is accessible to the target protein in solution as the solution contacts the chromatographic solid phase material. The target protein generally retains its specific binding affinity for the biospecific ligand during the chromatographic steps, while other solutes and/or proteins in the mixture do not bind appreciably or specifically to the ligand. Binding of the target protein to the immobilized ligand allows contaminating proteins or protein impurities to be passed through the chromatographic medium while the target protein remains specifically bound to the immobilized ligand on the solid phase material. The specifically bound target protein is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. Any component can be used as a ligand for purifying its respective specific binding protein, e.g. antibody. However, in various methods according to the present invention, Protein A is used as a ligand for an Fc region containing target protein. The conditions for elution from the biospecific ligand (e.g., Protein A) of the target protein (e.g., an Fc region containing protein) can be readily determined by one of ordinary skill in the art. In some embodiments, Protein G or Protein L or a functional variant thereof may be used as a biospecific ligand. In some embodiments, a biospecific ligand such as Protein A is used at a pH range of 5-9 for binding to an Fc region containing protein, washing or re-equilibrating the biospecific ligand/target protein conjugate, followed by elution with a buffer having pH about or below 4 which contains at least one salt.

The term "ion-exchange" and "ion-exchange chromatography" refers to the chromatographic process in which a solute or analyte of interest (e.g., an Fc region containing target protein) in a mixture interacts with a charged compound linked (such as by covalent attachment) to a solid phase ion exchange material such that the solute or analyte of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode ion exchange chromatography. For example, cation exchange chromatography can bind the target molecule (e.g., an Fc region containing target protein) followed by elution (cation exchange bind and elution chromatography or "CIEX") or can predominately bind the impurities while the target molecule "flows through" the column (cation exchange flow through chromatography FT-CIEX). Anion exchange chromatography can bind the target molecule (e.g., an Fc region containing target protein) followed by elution or can predominately bind the impurities while the target molecule "flows through" the column. In some embodiments and as demonstrated in the Examples set forth herein, the anion exchange chromatography step is performed in a flow through mode.

The phrase "ion exchange material" refers to a solid phase that is negatively charged (i.e. a cation exchange resin) or positively charged (i.e. an anion exchange resin). The charge may be provided by attaching one or more charged ligands to the solid phase, e.g. by covalent linking Alternatively, or in addition, the charge may be an inherent property of the solid phase (e.g. as is the case for silica, which has an overall negative charge).

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g., SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia).

A "mixed mode ion exchange resin" refers to a solid phase which is covalently modified with cationic, anionic, and hydrophobic moieties. A commercially available mixed mode ion exchange resin is BAKERBOND ABX™ (J. T. Baker, Phillipsburg, N.J.) containing weak cation exchange groups, a low concentration of anion exchange groups, and hydrophobic ligands attached to a silica gel solid phase support matrix.

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia).

The terms "Protein A" and "ProA" are used interchangeably herein and encompasses Protein A recovered from a native source thereof, Protein A produced synthetically (e.g., by peptide synthesis or by recombinant techniques), and variants thereof which retain the ability to bind proteins which have a $CH_2/CH_3$ region, such as an Fc region. Protein A can be purchased commercially from Repligen, Pharmacia and Fermatech. Protein A is generally immobilized on a solid phase support material. The term "ProA" also refers to an affinity chromatography resin or column containing chromatographic solid support matrix to which is covalently attached Protein A.

A functional derivative, fragment or variant of Protein A used in the methods according to the present invention may be characterized by a binding constant of at least $K=10^{-8}$ M, and preferably $K=10^{-9}$ M, for the Fc region of mouse IgG2a or human IgG1. An interaction compliant with such value for the binding constant is termed "high affinity binding" in the present context. Preferably, such functional derivative or variant of Protein A comprises at least part of a functional IgG binding domain of wild-type Protein A, selected from the natural domains E, D, A, B, C or engineered mutants thereof which have retained IgG binding functionality.

Also, Protein A derivatives or variants engineered to allow a single-point attachment may also be used in the affinity chromatography step in the claimed methods. Single point attachment generally means that the protein moiety is attached via a single covalent bond to a chromatographic support material of the Protein A affinity chromatography. Such single-point attachment may also occur by use of suitably reactive residues which are placed at an exposed amino acid position, namely in a loop, close to the N- or C-terminus or elsewhere on the outer circumference of the protein fold. Suitable reactive groups are e.g. sulfhydryl or amino functions.

A "contaminant Protein A" according to the present invention is any type of functional, IgG binding offspring of a Protein A or a functional derivative thereof as defined above which is obtained upon eluting bound antibody from a Protein A affinity chromatography column. Such contaminant Protein A species may result e.g. from hydrolysis of peptide bonds which is very likely to occur by means of enzyme action in particular in industrial manufacturing. Protein A chromatography is applied as an early step in downstream processing when the crudely purified, fresh product solution still harbors considerable protease activity. Dying cells in the cell culture broth or cells disrupted in initial centrifugation or filtration steps are likely to have set free proteases; for regulatory purposes, supplementation of the cell culture broth with protease inhibitors prior or in the course of downstream processing is usually not accomplished, in contrast to biochemical research practice. Examples are Phenyl-methyl-sulfonyl-chloride (PMSF) or e-caproic acid. Such chemical agents are undesirable as an additives in the production of biopharmaceuticals. It is further possible that recombinant functional derivatives or fragments of Protein A are less protease resistant than wild-type Protein A, depending on the tertiary structure of the protein fold. Amino acid segments linking individual IgG binding domains might be exposed once the total number of binding domains is reduced. Inter-domain contacts may possible contribute to the stability of domain folding. It might also be that binding of antibody by Protein A or said functional derivatives thereof influences or facilitates susceptibility to protease action, due to conformational changes induced upon binding of the antibody. Again, wild-type or full length Protein A or functional, engineered fragments thereof might behave differently.

By "binding" a molecule to an chromatography resin is meant exposing the molecule to chromatography resin under appropriate conditions (pH/conductivity) such that the molecule is reversibly immobilized in or on the chromatography resin by virtue of ligand—protein interactions. Non-limiting examples include ionic interactions between the molecule and a charged group or charged groups of the ion exchange material and a biospecific interaction between Protein A and an immunoglobulin.

The term "specific binding" as used herein, such as to describe interactions between a target protein (e.g., an Fc region containing protein) and a ligand bound to a solid support (e.g., Protein A bound to a solid phase matrix or resin), refers to the generally reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. Generally, the greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like. Ideally, in affinity chromatography specific binding occurs with an affinity of about $10^{-4}$ to $10^{-8}$ M in free solution.

The term "non-specific binding" as used herein, such as to describe interactions between a molecule of interest (e.g., a target protein has described herein) and a ligand or other compound bound to a solid support (e.g., Protein A bound to a solid phase matrix or resin), refers to binding of a protein of interest to the ligand or compound on a solid support through electrostatic forces, hydrogen bonding, hydrophobic forces, and/or van der Waals forces at an interaction site, but lacking structural complementarity that enhances the effects of the non-structural forces. Examples of non-specific interactions include, but are not limited to, electrostatic, hydrophobic, and van der Waals forces as well as hydrogen bonding.

A "salt" is a compound formed by the interaction of an acid and a base. Various salts which may be used in the buffers described herein include, but are not limited to, acetate (e.g. sodium acetate), citrate (e.g. sodium citrate), chloride (e.g. sodium chloride), sulphate (e.g. sodium sulphate), or a potassium salt.

As used herein, the term "solvent" refers to a liquid substance capable of dissolving or dispersing one or more other substances to provide a solution. Solvents include aqueous and organic solvents, where useful organic solvents include a non-polar solvent, ethanol, methanol, isopropanol, acetonitrile, hexylene glycol, propylene glycol, and 2,2-thiodiglycol.

The term "detergent" refers to ionic and nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), Useful detergents is a polysorbate, such as polysorbate 20 (TWEEN 20®.) or polysorbate 80 (TWEEN 80®.).

The term "polymer," as used herein, refers to a molecule formed by covalent linkage of two or more monomers, where the monomers are not amino acid residues. Examples of polymers include polyethyl glycol, polypropyl glycol, and copolymers (e.g. Pluronics, PF68 etc). A useful polymer is polyethylene glycol (PEG), e.g. PEG 400 and PEG 8000.

By "solid phase" or "porous substrates" or "base matrices" is meant a non-aqueous matrix to which one or more charged ligands can adhere. The solid phase may be a purification column, a discontinuous phase of discrete particles, a membrane, monolith or filter etc. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). In some steps of the methods of the claimed invention, a buffer has a pH in the range from 2.0 to 4.0, or from 2.8 to 3.8. In other steps of the claimed invention, a buffer has a pH in the range of 5.0 to 9.0. In other steps of the claimed invention, a buffer has a pH in the range of 4.0 to 6.5. In yet other steps of the methods of the claimed invention, a buffer has a pH lower than 4.0. Non-limiting examples of buffers that will control the pH in this range include MES, MOPS, MOPSO, Tris, HEPES, phosphate, acetate, citrate, succinate, and ammonium buffers, as well as combinations of these.

The term "cation exchange buffer" refers to equilibration buffers with a pH and conductivity such that the target molecule (e.g. immunoglobulin) will bind to the cation exchange material.

A "loading buffer" is a buffer which is used to load the sample or composition comprising the target molecule of interest (e.g., an Fc region containing target protein) and one or more impurities onto a chromatography column (e.g., an affinity column or an ion exchange column). The loading buffer has a conductivity and/or pH such that the molecule of interest (and generally one or more impurities) is/are bound to the chromatography resin or such that the protein of interest flows through the column while the impurities bind to the resin.

An "intermediate buffer" is used to elute one or more impurities from the chromatography resin, prior to eluting the polypeptide molecule of interest. The conductivity and/or pH of the intermediate buffer is/are such that one or more impurity is eluted from the ion exchange resin, but not significant amounts of the polypeptide of interest.

The term "wash buffer" or "equilibration buffer" are used interchangeably herein, refers to a buffer used to wash or re-equilibrate the chromatography resin prior to eluting the polypeptide molecule of interest. In some cases, the wash buffer and loading buffer may be the same.

An "elution buffer" is used to elute the target protein from the solid phase. The conductivity and/or pH of the elution buffer is/are usually such that the target protein is eluted from the chromatography resin.

A "regeneration buffer" may be used to regenerate the chromatography resin such that it can be re-used. The regeneration buffer has a conductivity and/or pH as required to remove substantially all impurities and the target protein from the chromatography resin.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSeimens per centimeter (mS/cm or mS), and can be measured using a conductivity meter sold, e.g., by Orion. The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Examples below.

The "pI" or "isoelectric point" of a polypeptide refer to the pH at which the polypeptide's positive charge balances its negative charge. pI can be calculated from the net charge of the amino acid residues or sialic acid residues of attached carbohydrates of the polypeptide or can be determined by isoelectric focusing.

By "washing" a chromatography media is meant passing an appropriate buffer through or over the media.

To "elute" a molecule (e.g., a polypeptide of interest or an impurity) from chromatography resin is meant to remove the molecule therefrom by altering the solution conditions such that buffer competes with the molecule of interest for the ligand sites on the chromatography resin. A non-limiting example is to elute a molecule from an ion exchange resin by altering the ionic strength of the buffer surrounding the ion exchange material such that the buffer competes with the molecule for the charged sites on the ion exchange material.

As used herein, "filtrate" refers to that portion of a sample that passes through the filtration membrane.

As used herein, "retentate" refers to that portion of a sample that is substantially retained by the filtration membrane.

The term "virus inactivation," "virus clearance," or "virus reduction," as used interchangeably herein, refers to any process which may render a virus incapable of infecting a cell or inhibit a virus function through a physico-chemical means. Typical virus inactivation methods include, but are not limited to, low pH treatment (e.g., below pH 4.5, below 4.0 or below 3.8), heat treatment, treatment with surfactants and radiation (e.g., ultraviolet light exposure). In some embodiments, virus inactivation methods are directed against retroviruses. In a particular embodiment, low pH conditions are used for virus inactivation as such conditions typically disrupt the virus lipid envelope, thereby inactivating the virus.

The term "low pH condition," as used herein, refers to a property of an aqueous solution or a buffer, where the pH of the solution or buffer is below the normal operating conditions, which are typically used for a cation exchange (CIEX) media loading of a sample containing an Fc region containing protein (e.g. monoclonal antibodies or MAbs). For example, typical CIEX loading conditions are above pH 4.5, and generally pH 5 to 6. In methods according to the present invention, a low pH condition may be used, e.g., a pH below 4.5.

The term "pre-elution step" refers to the penultimate chromatography step prior to elution, where the target molecule remains bound to the column, but the buffer mixing during loading onto the next column does not adversely effect target yield or target purity. Non-limiting examples include equilibrating a Protein A column loaded with an Fc containing protein in a buffer suitable for cation exchange column loading such as pH 5.4 sodium acetate or pH 5.0 sodium citrate, then elution of the column with pH 3 sodium acetate onto a cation exchange column.

Tangential flow filtration" or "TFF" or "crossflow filtration" refers to a filtration process in which the sample mixture circulates across the top of the membrane, while applied pressure causes certain solutes and small molecules to pass through the membrane. Typically, the solution flows parallel to the filter membrane. A pressure differential across the membrane causes fluid and filterable solutes to flow through the filter. This can be conducted as a continuous-flow process, since the solution is passed repeatedly over the membrane while that fluid that passes through the filter is continually drawn off into a separate circuit.

"High performance tangential flow filtration" or "HPTFF" refers to TFF performed at a flux between 5% and 100% of the transmembrane pressure on the flux versus transmembrane pressure curve (see, for example, U.S. Pat. Nos. 5,256,694; 4,490,937; and 6,054,051).

"Pore size distribution" refers, basically, to the number of pores having an actual radius, R, near some theoretical radius, r, expressed as the probability density function (see, Zeman, L. J. and Zydney, A. L., supra, p. 299-301). As the standard deviation of actual pore radii increases, the pore size distribution increases. Narrowed pore size distribution results from a reduction in the standard deviation of the pores from the theoretical value. This is achieved, for example, when the sizes of some of the larger pores are reduced by addition of charged compound into the larger pores of a charged membrane. The principle of liquid-liquid pore intrusion is useful for measuring pore size distribution (see R. van Reis and A. L. Zydney, supra, p. 2201). According to this principle, two highly immiscible liquids, such as solutions of a sulfate salt and a poly(ethylene glycol) are contacted through mixing to reach equilibrium partitioning. The membrane to be tested is primed with one of the liquids so that all pores are filled. After draining the feed channels, the second fluid is introduced into the system. The first fluid is then displaced out of the pores by the second fluid, and the flow rate is measured as a function of trans-membrane pressure. The resulting data provide information on pore size distribution and can be correlated with the nominal molecular weight cutoff (see R. van Reis and A. L. Zydney, supra, p. 2201).

Examples of "functional groups" include, but are not limited to, ion exchange groups, bioaffinity or biospecific groups, hydrophobic groups, thiophilic interaction groups, chelate or chelating groups, groups having so called pi-pi interactions with target compounds, hydrogen bonding groups, and hydrophilic groups.

Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Some preferred ligands that can be used herein include, but are not limited to, strong cation exchange groups, such as sulphopropyl, sulfonic acid; strong anion exchange groups, such as trimethylammonium chloride; weak cation exchange groups, such as carboxylic acid; weak anion exchange groups, such as N,N diethylamino or DEAE; hydrophobic interaction groups, such as phenyl, butyl, propyl, hexyl; and affinity groups, such as Protein A, Protein G, and Protein L.

II. Affinity Chromatography Step

In various embodiments according to the claimed invention, methods of the invention encompass the use of a Protein A based affinity resin for use in the affinity chromatography step. The Protein A can be native Protein A (from *Staph. Aureus*), recombinant Protein A or functional variant thereof. Examples of Protein A resins that may be used in the claimed processes include: ProSep-vA HC, ProSep Ultra Plus, Mab-Select, MabSelect SuRe and other commercially available affinity resins. Other affinity ligands/resins could be utilized in the methods described herein, such as, for example, Protein G and other Fc binding proteins (e.g., single chain camelid antibodies).

In the claimed methods, following the affinity capture step, the target protein is preferably eluted using pH 2.0 to 4.0, and preferably pH 2.8 to 3.8. The elution pool volume needs to be a volume large enough to remove the target protein from the affinity column and successfully load onto the subsequent in-line cation exchange column in the process. These volumes will vary depending on the relative size of the affinity and cation exchange columns. For example, if the affinity and cation exchange columns are of the same size, then the elution pool would preferably be eluted in 1-5 column volumes (CV), most preferably 1.5-4 CV. Non-limiting examples of affinity elution buffers are acetic acid, citric acid, phosphate and glysine. These affinity elution buffers can be modified with additional salts or additives to control conductivity or improve product recovery. For example, the additional components may contain additives to reduce aggregate formation. Non-limiting examples of additives include, but are not limited to, arginine, hexylene glycol and polyethylene glycol.

In some embodiments, an affinity capture step provides good loading capacity, product recovery and impurity removal for the subsequent ion exchange step(s).

III. Ion Exchange Chromatography Steps

In case of the methods described herein, the affinity step elution pool is directly loaded onto the cation exchange column, thereby eliminating the use of a holding tank/buffer exchange step. The cation exchange column can be equilibrated with a buffer ranging from pH 3.0 to 7.0, with conductivities ranging from 2-20 mS; and most preferably pH 4.5 to 6 having conductivities 2-16 mS. The column can be loaded with protein to 5-120 grams of target protein per liter of resin (g/L) in a single elution cycle from the affinity column or 5-120 g/L via multiple elution cycles of the affinity column. In some embodiments, the total loading on the cation exchange column is 20-80 g/L or 40-60 g/L.

The cation exchange column can be loaded with 1 or more cycles from the affinity capture step by re-equilibration the cation exchange column to a pH higher than the affinity elution pH after the loading.

In order to validate virus removal in the overall process, the CIEX column can be exchanged into a buffer with a pH less than 4.0 (e.g. <3.8) for viral inactivation for 10-60 minutes or 15-45 minutes after product loading. Alternatively, the column flow-through could be validated for virus removal at the loading pH, resulting in a cumulative virus removal for both virus flow-through and the reduced pH viral inactivation.

It has been observed that exposure of certain target protein to low pH conditions during or after protein loading or binding onto a column can influence the overall target protein recovery. The claimed invention provides improved methods of purification which avoid the loss of recovery by increasing conductivity of certain process steps. For example, the target protein recovery from the cation exchange step (CIEX) may be influenced by the low pH buffer steps during the purification process such as, for example, the Protein A elution step and virus inactivation steps, which are often carried out at low pH. In certain embodiments according to the claimed methods, an improved purification process is provided, which employs an increase in the conductivity of a low pH buffer, thereby improving the overall recovery of the target protein. Alternatively, the pH of a low pH buffer may be slightly increased (e.g., using a pH 4.5 vs. pH 3.5).

The conductivity of a low pH buffer can be increased, for example, by the addition of salt to the Protein A elution buffer or the virus inactivation buffer. The salt which may be used will depend on the pH of the buffer and can be readily identified by one of ordinary skill in the art. In some embodiments, the amount of salt added ranges from 25 mM to 500 mM and from 100 mM to 250 mM.

Elution of the cation exchange column can be accomplished using any of the steps described herein as well as those that are known in the art or those which may be readily determined by one of ordinary skill in the art. For example, in some embodiments, elution of the cation exchange column may be accomplished using one or more pH steps, where the eluate is directly loaded onto a anion exchange media in a flow-through mode. The elution pH change can also include changes to the buffer type, buffer concentration and salt concentration. The preferred range of elution pH for the cation exchange step described herein is from about 6.0 to 9.0, or from about 7.0 to 8.0.

Elution of the cation exchange column can also be accomplished using just an increase in buffer conductivity. The preferred range of elution conductivities depends on the pH and target molecules isoelectric point (pI). In general, elution is effective with conductivity changes ranging from 4 mS to 50 mS, or from 8 mS to 30 mS. The elution of the cation exchange column must be optimized to account for the performance of the subsequent anion exchange flow through step. For example, in some cases effective elution from the cation exchange step can be achieved, for example, by using a higher pH with low conductivity, such, for example, a 6 mS buffer at pH 7.0, or by using a lower pH with higher conductivity, such as, for example, a 15 mS buffer at pH 5.5. In these cases, the performance of the anion exchange flow through step should be explored with both conditions and the performance downstream of the cation exchange step determines the preferred elution method for cation exchange.

In some embodiments, a method according to the present invention includes a virus filtration step between and after any of the steps of the method, as appropriate. In some embodiments, the virus filtration step employs a prefilter, which can be of any format, including but not limited to, a membrane, depth filter, chromatography column or combinations thereof. The process can include additional clarification or depth filtration prior to the affinity capture using a membrane, depth filter, chromatography column or combinations thereof. Additional polishing steps can be added after the anion exchange, including but not limited to HPTFF, FT-HIC, HIC and others.

This invention is further illustrated by the following examples which should not be construed as limiting. The contents of all references, patents and published patent applications cited throughout this application, as well as the Figures, are incorporated herein by reference.

EXAMPLES

Example 1

Comparison of Binding Capacities of Resins for Low pH Loading

Three cation exchange media were compared for dynamic capacity under the conditions listed in Table 1 (typical elution conditions for Protein A affinity chromatography) using the following method.

Exemplary cation exchange media having the following characteristics were used: porous, mono-disperse polymethacrylate resin with a mean particle size of 60 μm, pore size between 60-80 nm, a "S" ligand density between 170-270 μmol/mL of resin and having pressure-flow properties such that a 20 cm bed height can reach >400 cm/hr at 2 bar and the IgG capacity is >50 g/L at 3 minute residence time, commercially ProRes-S™ from Millipore Corporation, Fractogel-S® from EMD Merck and SP-Sepharose Fast Flow® from GE Healthcare were packed into omnifit columns (0.66 cm diameter, 7 cm bed height) (Bio Chem Valve, Inc., Boontown, N.J.) and tested for dynamic binding capacity of polyclonal human gamma globulin (IgG). The columns were equilibrated with the pH and conductivity in Table 1, the conductivity was adjusted with sodium chloride as needed. The protein (5 g/L) was loaded onto the column with the protein in the same buffer as the equilibration buffer. The capacity at 5% breakthrough at a loading flow rate consistent with 3 minute residence time was used to characterize dynamic binding capacity.

TABLE 1

Summary of Binding Capacities for CIEX at Low pH.

| Binding Buffer Conditions | | ProRes-S™ (g/L) | Fractogel-S (g/L) | SP-Sepharose Fast Flow (g/L) |
|---|---|---|---|---|
| pH | Conductivity (mS) | | | |
| 3.5 | 6 | 52 | 53 | 21 |
| 3.8 | 6 | 53 | | 18 |
| 4.5 | 6 | 59 | | 34 |
| 5 | 6 | 56 | | 54 |

Example 2

Demonstration of Ion Exchange Steps Using a Model Feed under Direct Loading Conditions In a representative experiment, a model protein feed was used for demonstration of recovery and purification of protein following direct loading of a cation exchange column followed by an anion exchange step.

A model Protein A elution pool was designed using the following mixture: 50 mM sodium acetate buffer pH 3.5, 2.5 g/L polyclonal IgG, n-Protein A 50-100 ppm and 10% wt HCCF from a non-expressing CHO cell line. A 7 cm×0.66 cm omnifit column packed with ProRes-S™ was equilibrated with 50 mM acetate buffer at pH 3.5 (5 column volumes, CV). The model Protein A elution pool mixture (~20 mL) was loaded onto the ProRes-S™ column at 0.33 CV/min. After loading the protein mixture, the resin was then equilibrated with 3 CV of 100 mM citrate buffer at pH 5. Following equilibration at pH 5, the column was subsequently eluted with a series of pH steps starting with 50 mM Tris, pH 8.0 with 0.3M NaCl for 2 CV, followed by 50 mM Tris, pH 8.0 with 0.4M NaCl for 2 CV and 50 mM Tris, pH 8.0 with 0.5M NaCl for 2 CV. The elution volumes were loaded directly onto an exemplary anion exchange resin column (e.g., ProRes-S™ base media modified with anion exchange chemistry, as disclosed in US Patent Publication No. 20090050566), pre-equilibrated with 50 mM Tris, pH 8.0 with 0.3M NaCl and set in-line and downstream of the cation exchange column described above. The flow-through was collect in 2 CV fractions corresponding to the cation exchange elution steps. The flow-through fractions were pooled appropriately to form a "post chromatography pool" and assayed for key impurities, the results for which are summarized in Table 2.

TABLE 2

Ion Exchange (Polishing) Purification of Model Protein A Elution Pool

| | IgG Conc. (g/L) | Pool Vol. (mL) | HCP (ppm) | Pro A (ppm) | Aggregate (%) | Yield (%) |
|---|---|---|---|---|---|---|
| Model Protein A Elution Pool | 2.5 | 20 | 1746 | 63 | 3 | |

TABLE 2-continued

Ion Exchange (Polishing) Purification of Model Protein A Elution Pool

| | IgG Conc. (g/L) | Pool Vol. (mL) | HCP (ppm) | Pro A (ppm) | Aggregate (%) | Yield (%) |
|---|---|---|---|---|---|---|
| Post Chromatography Pool | 4 | 10 | 24 | 5 | 0* | 80 |

*Not Detectable

Example 3

A Batch Mode Process for Purifying an Fc Region Containing Protein

In a representative experiment, a batch mode process for purifying a monoclonal antibody, which is an exemplary Fc region containing protein, was designed, where the process uses a Protein A resin, a cation exchange resin with loading at different pH conditions and an anion exchange. The process is described as follows. This experiment demonstrated conditions that would allow for direct loading of ion exchange steps following affinity capture without the need for a holding tank or a buffer exchange step.

An IgG expressing line of Chinese Hamster Ovary (CHO) cells was incubated in a stirred bioreactor for approximately 10 days. The cells were removed using a primary depth filter (Millipore DOHC) followed by secondary clarification with a second depth filter (Millipore XOHC). The IgG1 was purified from the harvested clarified cell culture fluid (HCCF) the using the following procedure:

The affinity step employed the ProSep® Ultra Plus Protein A media (Millipore Corporation) and the Column Dimensions were as follows: Height=7 cm; I.D.=1 cm and Column Volume=5.5 mL.

TABLE 3.1

Procedure for Affinity Capture Step

| Step | Buffer | Residence Time (min) | CV |
|---|---|---|---|
| Equilibration (EQ) | 25 mM Tris, 25 mM NaCl, 0.05M EDTA, pH 8.0 | 3 | 5 |
| Load | HCCF | 3 | Load density 40 g/L |
| EQ | 25 mM Tris, 25 mM NaCl, 5 mM EDTA, pH 8.0 | 3 | 3 |
| Intermediate Wash | 0.2M Citrate, pH 5 | 3 | 3 |
| EQ | 25 mM Tris, 25 mM NaCl, 0.05M EDTA, pH 8.0 | 3 | 3 |
| Elution | 0.1M Acetic Acid, pH 2.8 | 3 | 3 |
| Regeneration | 0.15M Phosphoric Acid, approx. pH 1.5 | 3 | 3 |
| EQ | 25 mM Tris, 25 mM NaCl, 0.05M EDTA, pH 8.0 | 1 | 10 |

The Cation Exchange Chromatography step employed the ProRes-S™ media (Millipore Corporation) and the Column Dimensions were as follows: Height=22 cm; I.D.=0.66 cm and Column Volume=7.53 mL.

TABLE 3.2

General Procedure for CIEX Step

| Step | Buffer | Residence Time (min) | CV |
|---|---|---|---|
| Equilibration (EQ) | 0.025M MES, 50 mM NaCl pH 5.6 | 3 | 2 |
| Load | Adjusted ProA Pool (various pH) | 3 | Various, ~20 g/L |
| EQ | 0.025M MES, 50 mM NaCl pH 5.6 | 3 | 3 |
| Intermediate Wash | 0.025M MES, 70 mM NaCl pH 5.6 | 3 | 1 |
| EQ | 0.025M MES, 50 mM NaCl pH 5.6 | 3 | 3 |
| Elution | 0.025M MES, 500 mM NaCl pH 5.6 | 3 | >3, collect 2 mL pools |
| Strip | 0.025M MES, 1M NaCl pH 5.6 | 3 | 3 |
| EQ | 0.025M MES, 50 mM NaCl pH 5.6 | 1.4 | 6 |

The Anion Exchange Chromatography step employed the ChromaSorb® membrane (Millipore Corporation), in the ChromaSorb 0.08 mL device.

TABLE 3.3

General Procedure for FT-AIEX Step

| Step | Buffer | Flow Rate | Vol. or Duration |
|---|---|---|---|
| Pretreatment | 0.5M NaOH | 0.2 mL/min | 30 min |
| Equilibration (EQ) | 25 mM Tris, pH 8 | 1 mL/min | Check pH to 8.0 |
| Load | pH 8.0 adjusted/ diluted CEX Elution | 1 mL/min | 100 mL/Nano |

The columns were run independently and the pools from each step adjusted to mimic a potential direct transfer condition between columns. ProSep Ultra Plus was packed into a column as described above and loaded according to the steps in Table 3.1.

Figure 2:
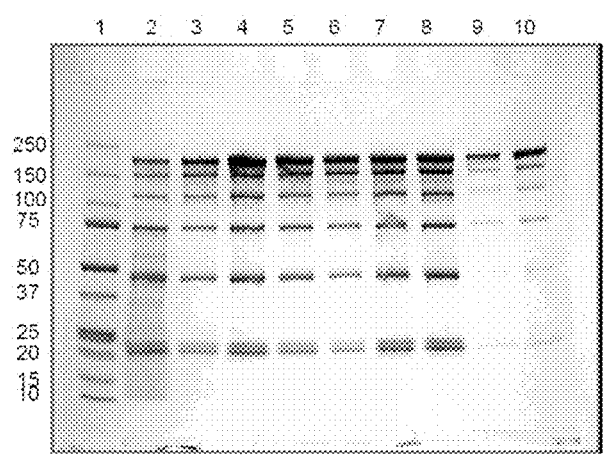
FIG. 2 depicts results from an SDS-PAGE experiment in which samples were analyzed under non-reducing conditions, as described in detail in Example 3. The dominant bands in all the lanes represent IgG. Intact IgG can be seen at ~175 kDa. Additional bands at 150 kDa, 100 kDa, 75 kDa, 40 kDa, and 20 kDa arise from partially reduced IgG, unassembled IgG or from IgG fragments.

The elution pool was generated at a range of pH values (pH 3.42, pH 3.44, pH 3.46 and pH 3.5) collected and the pH adjusted to create pools with a range of pH conditions for CIEX loading. Pools with pH adjustment to pH 3.41 (referred to as sample 1 herein), pH 3.75 (referred to as sample 2 herein), pH 4 (referred to as sample 3 herein), pH 4.3 (referred to as sample 4 herein) and pH 5.0 (referred to as sample 5 herein) were then loaded individually onto a cation exchange column (e.g., ProRes-S™) using the protocol described in Table 3.2 (see FIG. 1 for representative chromatograms). The elution pools from the cation exchange step were collected and pH adjusted to pH 8.0 before loading onto the anion exchange step (flow-through membrane adsorber ChromaSorb). The final pools were collected after the FT-AIEX step and assayed for purity and yield. The results are shown in Table 3.4 and Table 3.5 below. ChromaSorb yields were around 100% and expectedly unaffected by pH loading of ProRes-S™. The purity of the intermediate and final pools are shown in Table 3.6 below. Analysis of SDS PAGE gels for the corresponding pools are shown in FIG. 2. The feed was diluted 2-fold and the remaining samples were diluted 20-fold with Laemmli buffer.

TABLE 3.4

Yields for Affinity Capture Step

| Sample # | Load Density (mg/mL) | Experimental % Yield | ProA Elution Pool pH |
|---|---|---|---|
| 1 | 29.5 | ~100 | 3.42 |
| 2 | 29.5 | ~100 | 3.44 |
| 3 | 29.5 | ~100 | 3.46 |
| 4 | 29.5 | ~100 | 3.50 |
| 5 | 29.5 | ~100 | 3.50 |

TABLE 3.5

Yields for CIEX Step

| Sample # | Adjusted pH for CEX Loading | Load Density (mg/mL) | Volume (mL) | Experimental % Yield |
|---|---|---|---|---|
| 1 | 3.41 | 20 | 6 | 76.7 |
| 2 | 3.75 | 20 | 6 | 86.2 |
| 3 | 4 | 20 | 6 | 81.4 |
| 4 | 4.3 | 20 | 6 | 85.5 |
| 5 | 5 | 20 | 6 | 83.5 |

TABLE 3.6

Intermediate and Final Pool Purity for process described in Example 3.

| Sample # | Pool | SDS PAGE Lane[#] | HCP (ppm) | Pro A (ppm) | Aggregate (%) | Yield (%) |
|---|---|---|---|---|---|---|
|  | Feed | 2 | 9600 | NA | N/A | NA |
|  | Protein A Pool | 3 | 19 | 31 | 1 | ~100 |
| 1 | CIEX Pool (Loaded at pH 3.4) | 4 | 3 | 4 | 0.5 | 77 |
| 2 | CIEX Pool (Loaded at pH 3.75) | 5 | 5 | 5 | 0.2 | 86 |
| 3 | CIEX Pool (Loaded at pH 4) | 6 | 6 | 4 | 0.5 | 81 |
| 4 | CIEX Pool (Loaded at pH 4.3) | 7 | 5 | 5 | 0.4 | 85 |
| 5 | CIEX Pool (Loaded at pH 5) | 8 | 6 | 5 | 0.2 | 83 |
| 1 | Final Pool (ChromaSorb Pool from Sample 1) | 9 | <3* | <4* | NM | ~100 |
| 5 | Final Pool (ChromaSorb Pool from Sample 5) | 10 | <3* | 6 | NM | ~100 |
|  | Average Overall Process Yield |  |  |  |  | 82 |

*Below detection limit,
See FIG. 2 below,
NA = Not Applicable,
NM = Not Measured

Example 4

Purification Process Using Protein A Resin, Cation Exchange Resin and an Anion Exchange Resin without the Need for a Holding Tank and a Buffer Exchange Step In another representative experiment, an improved process was designed for the purification of an Fc region containing protein, e.g., a monoclonal antibody, which process employs a Protein A resin, a cation exchange resin and an anion exchange resin, without the need for a holding tank and a buffer exchange step.

Specifically, a clarified IgG containing feed was prepared according to the description in Example 3. The IgG1 was purified from the harvested clarified cell culture fluid (HCCF) the using the procedure described in Table 4, using the columns listed below.

The affinity step employed the Protein A Resin, ProSep Ultra Plus (Millipore Corporation), and the column had the following dimensions: Height=21 cm; I.D.=0.66 cm; and Column Volume=7.5 mL The Cation Exchange Chromatography step employed the ProRes-S media (Millipore Corporation) and having Column Dimensions as follows: Height=21 cm; I.D.=0.66 cm; and Column Volume=7.5 mL The Anion Exchange Resin used was the Q Sepharose Fast Flow (GE Healthcare) and the Column Dimensions were the following: Height=7 cm I.D.=0.66 cm and the Column Volume=2.4 mL

TABLE 4

Procedure for 3-Step Purification Process without holding tanks or buffer exchange steps

| Step | Buffer | Pro A Column | CIEX Column | AIEX Column | Column Volumes (CV)* | Residence Time (min) |
|---|---|---|---|---|---|---|
| AIEX Equilibration (AIEX EQ) | 25 mM Tris, 25 mM HEPES, 100 mM NaCl, pH 7.0 (AIEX EQ) | Offline | Offline | Inline | 3 | 3 |
| CIEX Equilibration (CIEX EQ) | 25 mM Sodium Acetate, 25 mM NaCl, pH | Offline | Inline | Offline | 3 | 3 |

TABLE 4-continued

Procedure for 3-Step Purification Process without holding tanks or buffer exchange steps

| Step | Buffer | Pro A Column | CIEX Column | AIEX Column | Column Volumes (CV)* | Residence Time (min) |
|---|---|---|---|---|---|---|
| ProA Equilibration (ProA EQ) | 5.4 (CIEX EQ) Phosphate Buffered Saline (PBS) pH 7.4 | Inline | Offline | Offline | 5 | 2.3 |
| ProA Loading | HCCF | Inline | Offline | Offline | 600 mL | 2.3 |
| ProA EQ Wash 1 | PBS | Inline | Offline | Offline | 3 | 2.3 |
| ProA Intermediate Wash 2 | 0.2M Citrate, pH 5.5 | Inline | Offline | Offline | 3 | 2.3 |
| ProA Equilibration with CIEX EQ | CIEX EQ | Inline | Offline | Offline | 3 | 4 |
| ProA Elution | 0.1M Acetic Acid, 150 mM NaCl, pH 3.5 | Inline | Inline | Offline | 3 | 4 |
| CIEX Equilibration | CIEX EQ | Offline | Inline | Offline | 4 | 2.3 |
| ProA Regeneration | 0.15M Phosphoric Acid | Inline | Offline | Offline | 3 | 2.3 |
| ProA EQ | PBS | Inline | Offline | Offline | 3 | 2.3 |
| CIEX EQ | CIEX EQ | Offline | Inline | Offline | 3 | 4 |
| CIEX Elution | 25 mM Tris, 25 mM HEPES, 100 mM NaCl, pH 7.0 | Offline | Inline | Inline (Collect Product Pool) | 7 | 4 |
| CIEX Regeneration | 0.5M NaOH | Offline | Inline | Offline | 3 | 4 |
| CIEX EQ | CIEX EQ | Offline | Inline | Offline | 3 | 4 |
| AIEX Regeneration | 0.5M NaOH | Offline | Offline | Inline | 3 | 3 |
| AIEX EQ | 25 mM Tris, 25 mM HEPES, 100 mM NaCl, pH 7.0 | Offline | Offline | Inline | 3 | 3 |

*For steps with 2 columns in-line, the CIEX column volume was used to determine buffer volumes (CV)

Figure 3:
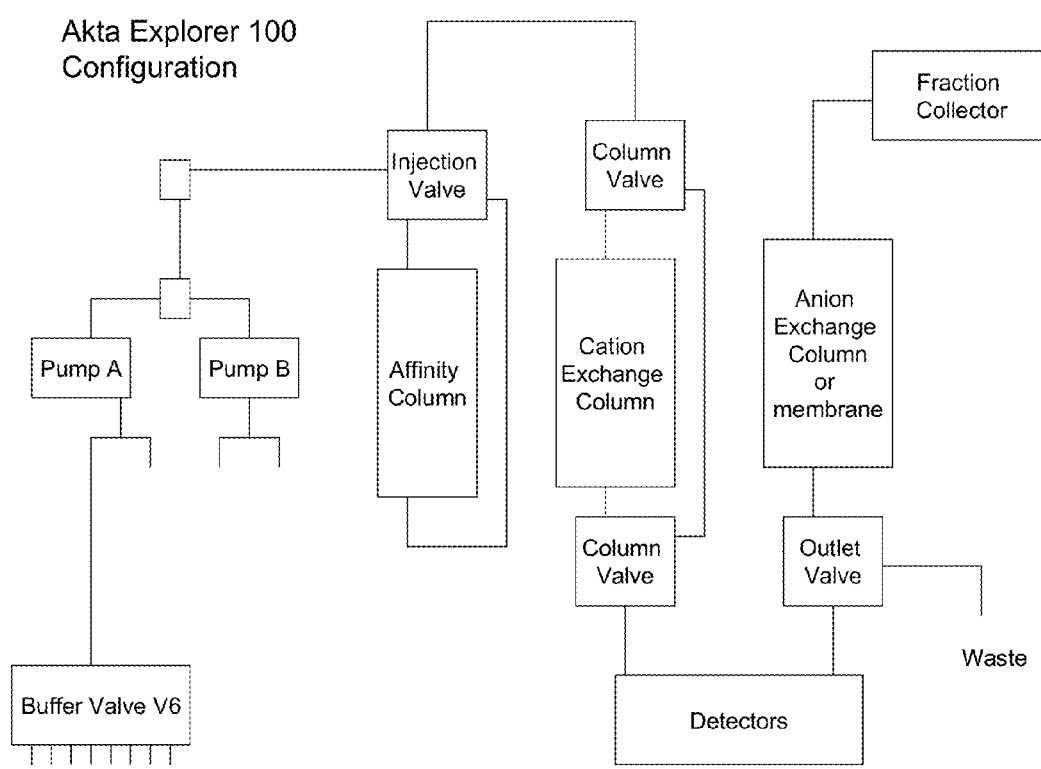
FIG. 3 depicts a schematic for a modified Akta (i.e., the chromatography work station or system) showing column plumbing for an in-line three step process.
Figure 4:
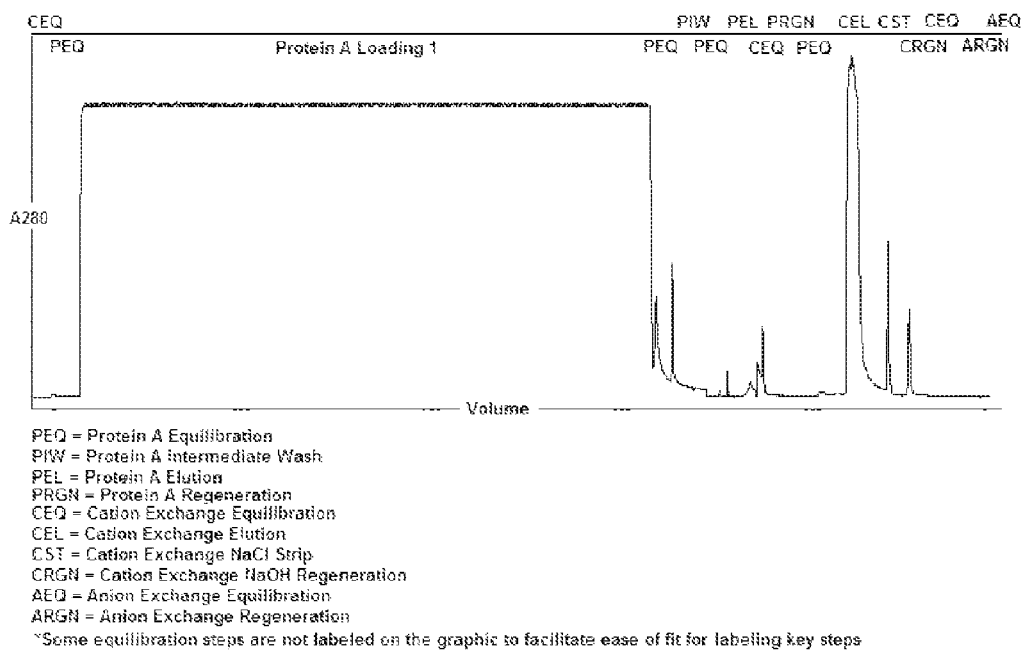
FIG. 4 depicts a chromatogram for direct loading of Protein A affinity media onto a cation exchange column.

The procedure described in Table 4 was run on an Akta explorer system (GE Healthcare) with the plumbing configuration shown in FIG. 3. The columns were run individually or coupled (in-line) as in the sequence described in Table 4. In this way, surprisingly, the IgG product could be purified without using holding tanks or buffer exchange. Without wishing to be bound by theory, it is contemplated that the chromatography column becomes the "holding tank" storing the product while the buffer is switched to a buffer which works as an elution buffer for the loaded column and a loading buffer for the next column down stream. The chromatograms are shown in FIG. 4. The purity and yield are characterized in Table 6.

Example 5

Purification Process Using Protein A Resin, Cation Exchange Resin and an Anion Exchange Membrane to Purify a Monoclonal Antibody without the Need for a Holding Tank or a Buffer Exchange Step A clarified IgG containing feed was prepared according to the description in Example 3. The IgG1 was purified from the harvested clarified cell culture fluid (HCCF) the using the procedure described in Table 4, using the columns listed below.

Protein A Resin used was the ProSep Ultra Plus (Millipore Corporation) having the column dimensions as follows: Height=21 cm; I.D.=0.66 cm; and Column Volume=7.5 mL The Cation Exchange Chromatography media used was the ProRes-S and having the column dimensions as follows: Height=21 cm; I.D.=0.66 cm; and column volume=7.5 mL.

The anion exchange membrane used was the ChromaSorb (Millipore Corporation) in the ChromaSorb 0.08 mL device The columns above were run as described for Example 4, except for the AIEX step which used a membrane adsorber instead of a resin column. The procedure described in Table 4 was run on an Akta explorer system with the plumbing configuration shown in FIG. 3. The columns were run individually or coupled (in-line) in the sequence described in Table 4. Consequently, surprisingly, the IgG product could be purified without using holding tanks or a buffer exchange step. The purity and yield are characterized in Table 6.

Example 6

Purification Process Using Multiple Cycles of a Protein A Resin, a Single Cycle of a Cation Exchange Resin and an Anion Exchange Membrane to Purify a Monoclonal Antibody A clarified IgG containing feed was prepared according to the description in Example 3. The IgG1 was purified from the harvested clarified cell culture fluid (HCCF) the using the procedure described in Table 5, using the columns listed below.

The Protein A Resin used was the ProSep Ultra Plus (Millipore Corporation) having the following column dimensions: height=12 cm; I.D.=0.66 cm; and Column Volume=4.1 mL The Cation Exchange Chromatography was performed using ProRes-S and having the following column dimensions: height=21 cm; I.D.=0.66 cm; and Column Volume=7.5 mL.

The Anion Exchange Membrane using ChromaSorb (Millipore Corporation) was used with a ChromaSorb 0.08 mL device.

TABLE 5

Procedure for 3-Step Purification Process without holding tanks or a buffer exchange step

| Process Step # | Step | Buffer | Pro A Column | CIEX Column | AIEX Column | CV* | Residence Time (min) |
|---|---|---|---|---|---|---|---|
| 1 | AIEX Equilibration (AIEX EQ) | 25 mM Tris, 25 mM HEPES, 100 mM NaCl, pH 7.0 (AIEX EQ) | Offline | Offline | Inline | 3 | 3 |
| 2 | CIEX Equilibration (CIEX EQ) | 25 mM Sodium Acetate, 25 mM NaCl, pH 5.4 (CIEX EQ) | Offline | Inline | Offline | 3 | 3 |
| 3 | ProA Equilibration (ProA EQ) | Phosphate Buffered Saline (PBS) pH 7.4 | Inline | Offline | Offline | 5 | 2.3 |
| 4 | ProA Loading | HCCF | Inline | Offline | Offline | 600 mL | 2.3 |
| 5 | ProA EQ Wash 1 | PBS | Inline | Offline | Offline | 3 | 2.3 |
| 6 | ProA Intermediate Wash 2 | 0.2M Citrate, pH 5.5 | Inline | Offline | Offline | 3 | 2.3 |
| 7 | ProA Equilibration with CIEX EQ | CIEX EQ | Inline | Offline | Offline | 3 | 4 |
| 8 | ProA Elution | 0.1M Acetic Acid, 150 mM NaCl, pH 3.5 | Inline | Inline | Offline | 3 | 4 |
| 9 | CIEX Equilibration | CIEX EQ | Offline | Inline | Offline | 4 | 2.3 |
| 10 | ProA Regeneration | 0.15M Phosphoric Acid | Inline | Offline | Offline | 3 | 2.3 |
| 11 | ProA EQ | PBS | Inline | Offline | Offline | 3 | 2.3 |
| Run second cycle on Protein A Column | | | | | | | |
| 4 | ProA Loading | HCCF | Inline | Offline | Offline | 600 mL | 2.3 |
| 5 | ProA EQ Wash 1 | PBS | Inline | Offline | Offline | 3 | 2.3 |
| 6 | ProA Intermediate Wash 2 | 0.2M Citrate, pH 5.5 | Inline | Offline | Offline | 3 | 2.3 |
| 7 | ProA Equilibration with CIEX EQ | CIEX EQ | Inline | Offline | Offline | 3 | 4 |
| 8 | ProA Elution | 0.1M Acetic Acid, 150 mM NaCl, pH 3.5 | Inline | Inline | Offline | 3 | 4 |

TABLE 5-continued

Procedure for 3-Step Purification Process without holding tanks or a buffer exchange step

| Process Step # | Step | Buffer | Pro A Column | CIEX Column | AIEX Column | CV* | Residence Time (min) |
|---|---|---|---|---|---|---|---|
| 9 | CIEX Equilibration | CIEX EQ | Offline | Inline | Offline | 4 | 2.3 |
| 10 | ProA Regeneration | 0.15M Phosphoric Acid | Inline | Offline | Offline | 3 | 2.3 |
| 11 | ProA EQ | PBS | Inline | Offline | Offline | 3 | 2.3 |
| 12 | CIEX EQ | CIEX EQ | Offline | Inline | Offline | 3 | 4 |
| 13 | CIEX Elution | 25 mM Tris, 25 mM HEPES, 100 mM NaCl, pH 7.0 | Offline | Inline | Inline (Collect Product Pool) | 7 | 4 |
| 14 | CIEX Regeneration | 0.5M NaOH | Offline | Inline | Offline | 3 | 4 |
| 15 | CIEX EQ | CIEX EQ | Offline | Inline | Offline | 3 | 4 |
| 16 | AIEX Regeneration | 0.5M NaOH | Offline | Offline | Inline | 3 | 3 |
| 17 | AIEX EQ | 25 mM Tris, 25 mM HEPES, 100 mM NaCl, pH 7.0 | Offline | Offline | Inline | 3 | 3 |

*For steps with 2 columns in-line, the CIEX column volume was used to determine buffer volumes (CV)

The columns above were run as described for Example 5, except the Protein A capture step was cycled 2× onto the cation exchange column (Repeat steps 4-11). The CIEX column was then eluted onto a membrane adsorber instead of a resin column. The procedure described in Table 6 was run on an Akta explorer system with the plumbing configuration shown in FIG. 3.

Figure 5:
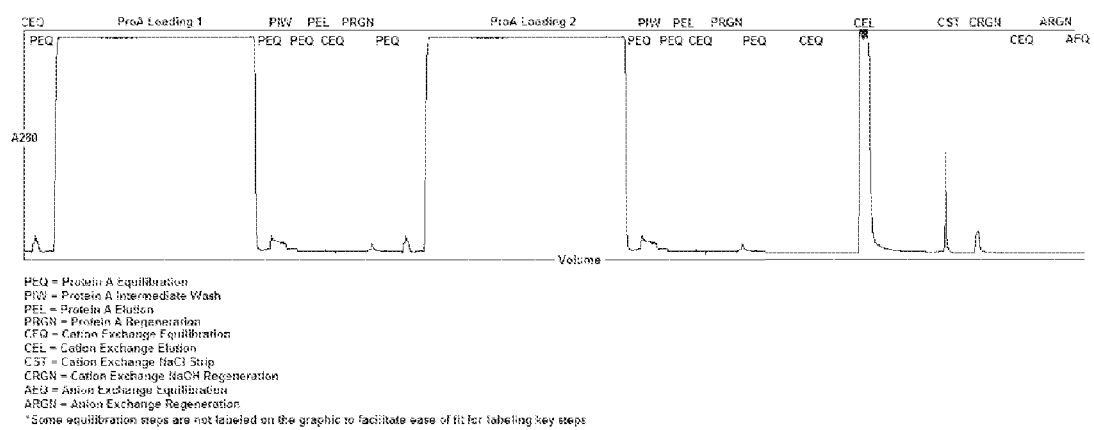
FIG. 5 depicts a chromatogram for loading 2 cycles of Protein A affinity capture steps onto a single in-line cation exchange column.

The columns were run individually or coupled (in-line) in the sequence described in Table 5. In this manner, the IgG product could be purified without using holding tanks or buffer exchange, thereby providing a more efficient and improved process. The chromatograms for loading 2 cycles of Protein A affinity elution on the cation exchange step is shown in FIG. 5. The purity and yield are characterized in Table 6.

Example 7

Purification Process Using Multiple Cycles of a Protein A Resin, a Single Cycle of a Cation Exchange Resin and an Anion Exchange Membrane to Purify a Monoclonal Antibody A clarified IgG containing feed was prepared according to the description in Example 3. The IgG1 was purified from the harvested clarified cell culture fluid (HCCF) the using the procedure described in Table 5, using the columns listed below.

The Protein A Resin used was the ProSep Ultra Plus (Millipore Corporation) and having the following column dimensions: Height=5 cm; I.D.=0.66 cm; and Column Volume=2 mL.

The Cation Exchange Chromatography step used the ProRes-S media (Millipore Corporation) and the Column Dimensions as follows: Height=21 cm; I.D.=0.66 cm; and Column Volume=7.5 mL.

The Anion Exchange Membrane used was the ChromaSorb (Millipore Corporation) in the ChromaSorb 0.08 mL device.

The columns described above were run as described for Example 6, except the Protein A capture step was cycled a total of 4× onto the cation exchange column (Steps 4-11 were run 4 successive times before cation elution). The procedure described in Table 6 was run on an Akta explorer system with the plumbing configuration shown in FIG. 3. The columns were run individually or coupled (in-line) in the sequence described in Table 6.

Figure 6:
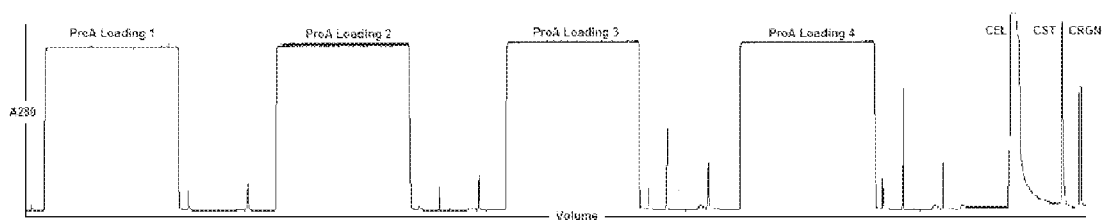
FIG. 6 depicts a chromatogram for loading 4 cycles of Protein A affinity capture steps onto a single in-line cation exchange column.

Consequently, surprisingly, the IgG product could be purified without using holding tanks or a buffer exchange step. The chromatograms for loading 4 cycles of Protein A affinity elution on the cation exchange step is shown in FIG. 6. The purity and yield are characterized in Table 6.

TABLE 6

Final Pool Purity for process described in Examples 4-7

| Example | Pool | SDS PAGE Lane# | HCP (ppm) | DNA Purification Factor** | Yield (%) |
|---|---|---|---|---|---|
| | Feed | 2 | 9700 | 0.7 ug/mL | NA |
| Example 4 | Final Pool | 7, 8 | <3* | 4 | 83 |
| Example 5 | Final Pool | 9, 10 | <3* | 15 | 80 |
| Example 6 | Final Pool | 11 | <3* | 9 | 71 |
| Example 7 | Final Pool | 12, 13 | <3* | 7 | 71 |
| | Average Overall Process Yield | | | | 76 |

Figure 7:
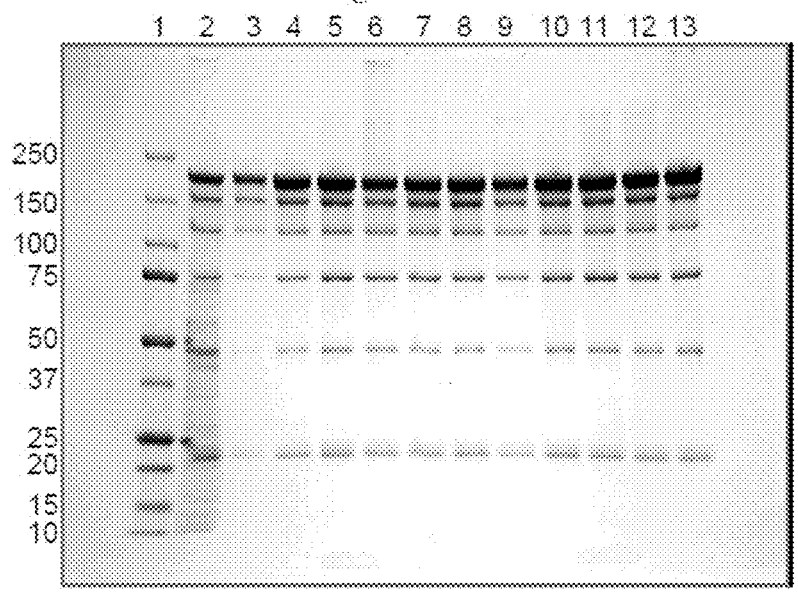
FIG. 7 depicts results from an SDS-PAGE experiment, as described in detail in Examples 4-7. The dominant bands in all the lanes represent IgG. The samples were analyzed under reducing and non-reducing conditions. Intact IgG can be seen at ~175 kDa. Additional bands at 150 kDa, 100 kDa, 75 kDa, 40 kDa, and 20 kDa arise from partially reduced IgG, unassembled IgG or from IgG fragments.
Figure 7:
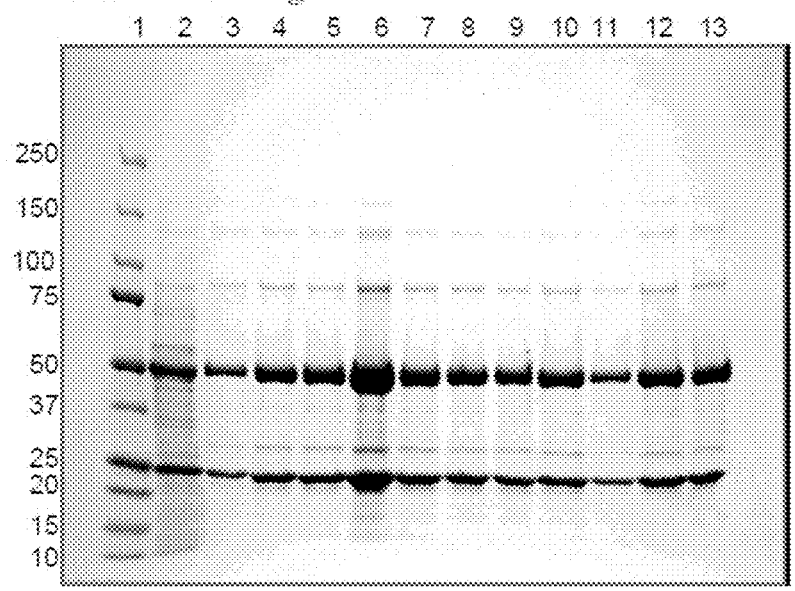

*Below detection limit, # See FIG. 7 below,
NA = Not Applicable,
NM = Not Measured,
**Purification Factor = [DNA] in Feed/[DNA] in final pool. Purification factor (ppm load/ppm final pool) is reported because of limitations of the DNA assay.

Example 8

Purification Process Using a Single Cycle of a Protein A Resin, a Single Cycle of a Cation Exchange Resin and an Anion Exchange Resin to Purify a Monoclonal Antibody A clarified IgG containing feed was prepared according to the description in Example 3. The IgG1 was purified from the harvested clarified cell culture fluid (HCCF) the using the procedure described in Table 7, using the columns listed below.

The Protein A Resin used was the ProSep Ultra Plus (Millipore Corporation) and having the following Column Dimensions: Height=21 cm; I.D.=0.66 cm; and Column Volume=7.5 mL The Cation Exchange Chromatography step employed the ProRes-S media (Millipore Corporation) and the following Column Dimensions: Height=21 cm; I.D.=0.66 cm; and Column Volume=7.5 mL.

The Anion Exchange Resin used was the Q Sepharose Fast Flow (GE Healthcare), having the following Column Dimensions: Height=5 cm; I.D.=1.1 cm; and Column Volume=4.8 mL.

TABLE 7

Procedure for 3-Step Purification Process without holding tanks or a buffer exchange step

| Process Step # | Step | Buffer | Pro A Column | CIEX Column | AIEX Column | Column Volumes (CV)* | Residence Time (min) |
|---|---|---|---|---|---|---|---|
| 1 | AIEX Equilibration (AIEX EQ) | 25 mM Tris, 25 mM HEPES, 100 mM NaCl, pH 7.0 (AIEX EQ) | Offline | Offline | Inline | 3 | 3 |
| 2 | CIEX Equilibration (CIEX EQ) | 25 mM Sodium Acetate, 25 mM NaCl, pH 5.4 (CIEX EQ) | Offline | Inline | Offline | 3 | 3 |
| 3 | ProA Equilibration (ProA EQ) | Phosphate Buffered Saline (PBS) pH 7.4 | Inline | Offline | Offline | 5 | 2.3 |
| 4 | ProA Loading | HCCF | Inline | Offline | Offline | 600 mL | 2.3 |
| 5 | ProA EQ Wash 1 | PBS | Inline | Offline | Offline | 3 | 2.3 |
| 6 | ProA Intermediate Wash 2 | 0.2M Citrate, pH 5.5 | Inline | Offline | Offline | 3 | 2.3 |
| 7 | ProA Equilibration with CIEX EQ | CIEX EQ | Inline | Offline | Offline | 3 | 4 |
| 8 | ProA Elution | 0.1M Acetic Acid, 150 mM NaCl, pH 3.5 | Inline | Inline | Offline | 4 | 4 |
| 9 | CIEX Equilibration | CIEX EQ | Offline | Inline | Offline | 4 | 2.3 |
| 10 | ProA Regeneration | 0.15M Phosphoric Acid | Inline | Offline | Offline | 3 | 2.3 |
| 11 | ProA EQ | PBS | Inline | Offline | Offline | 3 | 2.3 |
| 12 | CIEX EQ | CIEX EQ | Offline | Inline | Offline | 3 | 4 |
| 13 | CIEX Elution | 25 mM Tris, 25 mM HEPES, 100 mM NaCl, pH 7.0 | Offline | Inline | Inline (Collect Product Pool) | 7 | 4 |
| 14 | CIEX Regeneration | 0.5M NaOH | Offline | Inline | Offline | 3 | 4 |
| 15 | CIEX EQ | CIEX EQ | Offline | Inline | Offline | 3 | 4 |
| 16 | AIEX Regeneration | 0.5M NaOH | Offline | Offline | Inline | 3 | 3 |
| 17 | AIEX EQ | 25 mM Tris, 25 mM HEPES, 100 mM | Offline | Offline | Inline | 3 | 3 |

TABLE 7-continued

Procedure for 3-Step Purification Process without holding tanks or a buffer exchange step

| Process Step # | Step | Buffer | Pro A Column | CIEX Column | AIEX Column | Column Volumes (CV)* | Residence Time (min) |
|---|---|---|---|---|---|---|---|
| | | NaCl, pH 7.0 | | | | | |

*For steps with 2 columns in-line, the CIEX column volume was used to determine buffer volumes (CV)

The columns above were run using the procedure described in Table 7 on an Akta explorer system with the plumbing configuration shown in FIG. 3. The columns were run individually or couple (in-line) in the sequence described in Table 7. Consequently, the IgG product was purified without using holding tanks or buffer exchange.

The purity and yield are characterized in Table 9.

Example 9

Process Using a Single Cycle of a Protein A Resin, a Single Cycle of a Cation Exchange Resin and an Anion Exchange Membrane to Purify a Monoclonal Antibody A clarified IgG containing feed was prepared according to the description in example 3. The IgG1 was purified from the harvested clarified cell culture fluid (HCCF) the using the procedure described in Table 7, using the columns listed below.

The Protein A Resin used was the ProSep Ultra Plus (Millipore Corporation) having the following Column Dimensions: Height=21 cm; I.D.=0.66 cm; and Column Volume=7.5 mL.

The Cation Exchange Chromatography step used the ProRes-S media (Millipore Corporation) and the following Column Dimensions: Height=21 cm; I.D.=0.66 cm; and Column Volume=7.5 mL.

The following Anion Exchange Membrane was used: ChromaSorb (Millipore Corporation) in a ChromaSorb 0.08 mL device.

The columns above were run, as described above for Example 8. The procedure described in Table 7 was run on an Akta explorer system with the plumbing configuration shown in FIG. 3. The columns were run individually or coupled (in-line) in the sequence described in Table 7.

Consequently, the IgG product was purified without using holding tanks or a buffer exchange step. The purity and yield are characterized in Table 9.

Example 10

Purification Process Using Multiple Cycles of a Protein A Resin, a Single Cycle of a Cation Exchange Resin and a Mixed Mode Resin to Purify a Monoclonal Antibody A clarified IgG containing feed was prepared according to the description in Example 3. The IgG1 was purified from the harvested clarified cell culture fluid (HCCF) the using the procedure described in Table 8, using the columns listed below.

The Protein A media used was the ProSep Ultra Plus Resin (Millipore Corporation) having the following Column Dimensions: Height=5 cm; I.D.=0.66 cm; and Column Volume=2 mL.

The cation exchange chromatography media used was the ProRes-S (Millipore Corporation), having the following column dimensions: Height=21 cm; I.D.=0.66 cm; and Column Volume=7.5 mL.

The anion exchange chromatography media was a mixed mode resin using Capto Adhere (GE Healthcare) having the following column dimensions: Height=5 cm; I.D.=0.66 cm; and Column Volume=2 mL The columns described above were run as described for Example 6, except the Protein A capture step was cycled a total of 4× onto the cation exchange column (Steps 4-11 were run 4 successive times before cation elution). The procedure described in Table 8 was run on an Akta explorer system with the plumbing configuration shown in FIG. 3. The columns were run individually or coupled (in-line) in the sequence described in Table 8. In this way, surprisingly, the IgG product could be purified without using holding tanks or a buffer exchange step. The purity and yield are characterized in Table 9.

TABLE 8

Procedure for 3-Step Purification Process without holding tanks or a buffer exchange step

| Process Step # | Step | Buffer | Pro A Column | CIEX Column | AIEX Column | (CV)* | Residence Time (min) |
|---|---|---|---|---|---|---|---|
| 1 | AIEX Equilibration (AIEX EQ) | 25 mM Tris, 25 mM HEPES, 100 mM NaCl, pH 7.0 (AIEX EQ) | Offline | Offline | Inline | 3 | 3 |
| 2 | CIEX Equilibration (CIEX EQ) | 25 mM Sodium Acetate, 25 mM NaCl | Offline | Inline | Offline | 3 | 3 |

TABLE 8-continued

Procedure for 3-Step Purification Process without holding tanks or a buffer exchange step

| Process Step # | Step | Buffer | Pro A Column | CIEX Column | AIEX Column | (CV)* | Residence Time (min) |
|---|---|---|---|---|---|---|---|
| 3 | ProA Equilibration (ProA EQ) | pH 5.4 (CIEX EQ) Phosphate Buffered Saline (PBS) pH 7.4 | Inline | Offline | Offline | 5 | 2.3 |
| 4 | ProA Loading | HCCF | Inline | Offline | Offline | 600 mL | 2.3 |
| 5 | ProA EQ Wash 1 | PBS | Inline | Offline | Offline | 3 | 2.3 |
| 6 | ProA Intermediate Wash 2 | 0.2M Citrate, pH 5.5 | Inline | Offline | Offline | 3 | 2.3 |
| 7 | ProA Equilibration with CIEX EQ | CIEX EQ | Inline | Offline | Offline | 3 | 4 |
| 8 | ProA Elution | 0.1M Acetic Acid, 150 mM NaCl, pH 3.5 | Inline | Inline | Offline | 3 | 4 |
| 9 | CIEX Equilibration | CIEX EQ | Offline | Inline | Offline | 4 | 2.3 |
| 10 | ProA Regeneration | 0.15M Phosphoric Acid | Inline | Offline | Offline | 3 | 2.3 |
| 11 | ProA EQ | PBS | Inline | Offline | Offline | 3 | 2.3 |
| Run second, third and fourth cycle on Protein A Column | | | | | | | |
| 4 | ProA Loading | HCCF | Inline | Offline | Offline | 600 mL | 2.3 |
| 5 | ProA EQ Wash 1 | PBS | Inline | Offline | Offline | 3 | 2.3 |
| 6 | ProA Intermediate Wash 2 | 0.2M Citrate, pH 5.5 | Inline | Offline | Offline | 3 | 2.3 |
| 7 | ProA Equilibration with CIEX EQ | CIEX EQ | Inline | Offline | Offline | 3 | 4 |
| 8 | ProA Elution | 0.1M Acetic Acid, 150 mM NaCl, pH 3.5 | Inline | Inline | Offline | 3 | 4 |
| 9 | CIEX Equilibration | CIEX EQ | Offline | Inline | Offline | 4 | 2.3 |
| 10 | ProA Regeneration | 0.15M Phosphoric Acid | Inline | Offline | Offline | 3 | 2.3 |
| 11 | ProA EQ | PBS | Inline | Offline | Offline | 3 | 2.3 |
| 12 | CIEX EQ | CIEX EQ | Offline | Inline | Offline | 3 | 4 |
| 13 | CIEX Elution | 25 mM Tris, 25 mM HEPES, 100 mM NaCl, pH 7.0 | Offline | Inline | Inline (Collect Product Pool) | 7 | 4 |
| 14 | CIEX Regeneration | 0.5M NaOH | Offline | Inline | Offline | 3 | 4 |
| 15 | CIEX EQ | CIEX EQ | Offline | Inline | Offline | 3 | 4 |
| 16 | AIEX Regeneration | 0.5M NaOH | Offline | Offline | Inline | 3 | 3 |
| 17 | AIEX EQ | 25 mM Tris, 25 mM HEPES, 100 mM NaCl, pH 7.0 | Offline | Offline | Inline | 3 | 3 |

*For steps with 2 columns in-line, the CIEX column volume was used to determine buffer volumes (CV)

Example 11

Purification Process Using a Single Cycle of a Protein A Resin, a Single Cycle of a Cation Exchange Resin Including an Anion Exchange Media to Purify a Monoclonal Antibody A clarified IgG containing feed was prepared according to the description in example 3. The IgG1 was purified from the harvested clarified cell culture fluid (HCCF) the using the procedure described in Table 7, using the columns listed below.

Protein A media used was the MabSelect® SuRe (GE Healthcare) having the Column Dimensions Height=21 cm; I.D.=0.66 cm; and Column Volume=7.5 mL.

The Cation Exchange Chromatography used was the ProRes-S (Millipore Corporation) having the Column Dimensions: Height=21 cm; I.D.=0.66 cm; and Column Volume=7.5 mL.

The Anion Exchange Membrane used was the ChromaSorb (Millipore Corporation) with a ChromaSorb 0.08 mL device.

The columns above were run as for example 8. The procedure described in Table 7 was run on an Akta explorer system with the plumbing configuration shown in FIG. 3. The columns were run individually or coupled (in-line) in the sequence described in Table 7. In this way the IgG product could be purified without using holding tanks or buffer exchange. The purity and yield are characterized in Table 9.

The Cation Exchange Chromatography step used ProRes-S (Millipore Corporation) having the following Column Dimensions: Height=21 cm; I.D.=0.66 cm; and Column Volume=7.5 mL The Anion Exchange Chromatography step employed ChromaSorb (Millipore Corporation) with a ChomaSorb 0.08 mL device.

The columns above were run as described for Example 8. The procedure described in Table 7 was run on an Akta explorer system with the plumbing configuration shown in FIG. 3. The columns were run individually or coupled (in-line) in the sequence described in Table 7. In this way, surprisingly, the IgG product could be purified without using holding tanks or buffer exchange. The purity and yield are characterized in Table 11.

Example 13

Purification Process Using a Single Cycle of a Protein A Resin, a Single Cycle of a Cation Exchange Resin Including a 30 Minute Low pH Hold and an Anion Exchange Membrane to Purify a Monoclonal Antibody A clarified IgG containing feed was prepared according to the description in Example 3. The IgG1 was purified from the

TABLE 9

Final pool purity for process described in Examples 8-11.

| Example | Pool | Aggregate (%) | HCP (ppm) | ProA (ppm) | DNA Purification Factor** | yield (%) |
|---|---|---|---|---|---|---|
| | Feed | 3.7 | 9700 | NA | 0.7 ug/mL | NA |
| Example 8 | Final Pool | 1.7 | <3* | <4* | NM | 72 |
| Example 9 | Final Pool | 2.3 | <3* | <4* | 13 | 83 |
| Example 10 | Final Pool | 2.4 | <3* | <4* | 74 | 51# |
| Example 11 | Final Pool | 0.9 | <3* | NM | 25 | 89 |

*Below detection limit,
NA = Not Applicable,
NM = Not Measured,
**Purification Factor = [DNA] in Feed/[DNA] in final pool. Purification factor is reported because of limitations of the DNA assay (ppm load/ppm final pool).
Conditions were not optimal for this resin according to manufacturer recommendations, Yield could be improved by performing the separation closer to manufacturer recommended conditions.

Example 12

Purification Process Using a Single Cycle of a Protein A Resin, a Single Cycle of a Cation Exchange Resin with No Low pH Hold and an Anion Exchange Membrane to Purify a Monoclonal Antibody A clarified IgG containing feed was prepared according to the description in example 3. The IgG1 was purified from the harvested clarified cell culture fluid (HCCF) the using the procedure described in Table 7, using the columns listed below.

Protein A Resin used was the ProSepUltra Plus (Millipore Corporation) with the following Column Dimensions: Height=21 cm; I.D.=0.66 cm; and Column Volume=7.5 mL.

harvested clarified cell culture fluid (HCCF) the using the procedure described in Table 10, using the columns listed below.

The affinity step used the Protein A Resin, ProSep Ultra Plus (Millipore Corporation) having the Column Dimensions: Height=21 cm; I.D.=0.66 cm; and Column Volume=7.5 mL.

The Cation Exchange Chromatography step used the ProRes-S media (Millipore Corporation) having the Column Dimensions: Height=21 cm; I.D.=0.66 cm; and Column Volume=7.5 mL.

The Anion Exchange Chromatography step used the ChromaSorb membrane with the ChromaSorb 0.08 mL device (Millipore Corporation).

TABLE 10

Procedure for 3-Step Purification Process without holding tanks or a buffer exchange step

| Process Step # | Step | Buffer | Pro A Column | CIEX Column | AIEX Column | Column Volumes (CV)* | Residence Time (min) |
|---|---|---|---|---|---|---|---|
| 1 | AIEX Equilibration (AIEX EQ) | 25 mM Tris, 25 mM HEPES, 100 mM NaCl, pH 7.0 (AIEX EQ) | Offline | Offline | Inline | 3 | 3 |
| 2 | CIEX Equilibration (CIEX EQ) | 25 mM Sodium Acetate, 25 mM NaCl pH, 5.4 (CIEX EQ) | Offline | Inline | Offline | 3 | 3 |
| 3 | ProA Equilibration (ProA EQ) | Phosphate Buffered Saline (PBS) pH 7.4 | Inline | Offline | Offline | 5 | 2.3 |
| 4 | ProA Loading | HCCF | Inline | Offline | Offline | 600 mL | 2.3 |
| 5 | ProA EQ Wash 1 | PBS | Inline | Offline | Offline | 3 | 2.3 |
| 6 | ProA Intermediate Wash 2 | 0.2M Citrate, pH 5.5 | Inline | Offline | Offline | 3 | 2.3 |
| 7 | ProA Equilibration with CIEX EQ | CIEX EQ | Inline | Offline | Offline | 3 | 4 |
| 8 | ProA Elution | 0.1M Acetic Acid, 150 mM NaCl, pH 3.5 | Inline | Inline | Offline | 6 | 4 |
| 9 | Low pH Hold | 0.1M Acetate pH, 150 mM NaCl, 3.6 | Offline | Inline | Offline | Minimum 0.5 (exposure time = 30 minutes) | 60 (reduce flow rate) |
| 10 | CIEX Elution | 25 mM Tris, 25 mM HEPES, 100 mM NaCl, pH 7.0 | Offline | Inline | Inline (Collect Product Pool) | 7 | 4 |
| 11 | CIEX Equilibration | CIEX EQ | Offline | Inline | Offline | 4 | 2.3 |
| 12 | ProA Regeneration | 0.15M Phosphoric Acid | Inline | Offline | Offline | 3 | 2.3 |
| 13 | ProA EQ | PBS | Inline | Offline | Offline | 3 | 2.3 |
| 14 | CIEX EQ | CIEX EQ | Offline | Inline | Offline | 3 | 4 |
| 15 | CIEX EQ | CIEX EQ | Offline | Inline | Offline | 3 | 4 |
| 16 | CIEX Regeneration | 0.5M NaOH | Offline | Inline | Offline | 3 | 4 |
| 17 | CIEX EQ | CIEX EQ | Offline | Inline | Offline | 3 | 4 |
| 18 | AIEX Regeneration | 0.5M NaOH | Offline | Offline | Inline | 3 | 3 |
| 19 | AIEX EQ | 25 mM Tris, 25 mM HEPES, 100 mM NaCl, pH 7.0 | Offline | Offline | Inline | 3 | 3 |

*For steps with 2 columns in-line, the CIEX column volume was used to determine buffer volumes (CV)

The columns above were run using the procedure in Table 10. The procedure described in Table 10 was run on an Akta explorer system with the plumbing configuration shown in FIG. 3. Consequently, surprisingly, the IgG product could be purified without using holding tanks or buffer exchange steps. The purity and yield are characterized in Table 11.

Example 14

Demonstration of Inventive Process Using a Single Cycle of a Protein A Resin, a Single Cycle of a Cation Exchange Resin Including a 1 Hour Low pH Hold and an Anion Exchange Membrane to Purify a Monoclonal Antibody The columns described in Example 13 were run using the procedure in Table 10, with the exception that the low pH hold step exposure time was increase to 1 hour as compared to 30 minutes in Example 13. The procedure described in Table 10 was run on an Akta explorer system with the plumbing configuration shown in FIG. 3. In this way, the IgG product could be purified without using holding tanks or a buffer exchange step. The purity and yield are characterized in Table 11.

TABLE 11

Product recovery and purity for inventive process with low pH hold

| Example | Pool | Aggregate (%) | HCP (ppm) | ProA (ppm) | Yield (%) |
|---|---|---|---|---|---|
| | Feed | 2.4 | 300,000 | NA | NA |
| Example 12 | Final Pool | 1.4 | <3* | <4* | 78 |
| Example 13 | Final Pool | 1.3 | <3* | <4* | 72 |
| Example 14 | Final Pool | 1.4 | <3* | <4* | 73 |

Example 15

Purification Process Using a Single Cycle of a Protein A Resin, Collected as Pool and then Spike with Virus, Followed by a Single Cycle of a Cation Exchange Resin Including a Low pH Hold to Inactivate Virus on the Cation Exchange Column A clarified IgG containing feed was prepared according to the description in Example 3. The IgG1 was purified from the harvested clarified cell culture fluid (HCCF) using a ProSep Ultra Plus column similar to the procedure described in Table 3.1 with the exception of the equilibration buffer being 25 mM Tris, 25 mM NaCl, 0.05M EDTA, pH 7.0 and the elution buffer being 100 mM Acetic acid, 150 mM NaCl, pH 3.5. The Protein A column elution was titrated to pH 4.0 in order to approximate the direct loading of the elution pool from Protein A onto the cation exchange column. A virus spike of 6.5 Log X-MuLV (5% spike, Murine Leukemia Virus) was added to the pool. The pool was then run through a ProRes-S cation exchange column under conditions described in Table 12. Relevant fractions were assayed for X-MuLV via an infectivity assay and qPCR using standard methods and protocols well known in the art. The low pH hold wash and column regeneration showed ≧3.5 log reduction in virus infectivity and no active virus was detected. The product elution pool showed ≧4.3 log reduction in virus infectivity and no active virus was detected. Therefore, virus inactivation with a low pH hold on the CIEX column is an effective way to reduce virus activity below detectable levels. In order to claim higher levels of removal, the virus spiking strategy and assay would need to be refined to improve resolution.

TABLE 12

Chromatography steps and buffer conditions for virus spiking experiment

| Chromatography Step | Buffer | Column Volumes (CV) | Residence Time (minutes) | Virus Conc. (Log) |
|---|---|---|---|---|
| CIEX EQ | 50 mM Sodium Acetate, 25 mM NaCl, pH 5.4 | 4 | 3 | |
| Load | Protein A Pool titrated to pH 4 | 6 (load density = 50 mg/mL) | 3 | 6.5 |
| CIEX Wash | 50 mM Sodium Acetate, 150 mM NaCl, pH 3.5 | 3 | 3 | |
| Low pH Hold | 50 mM Sodium Acetate, 150 mM NaCl, pH 3.5 | 0.5 (Total step time = 0.5 hr) | 60 | ≦2.8 |
| CIEX Elution | 50 mM Sodium Acetate, 175 mM NaCl, pH 5.4 | 6* | 3 | ≦2.2 |
| Column Regeneration | 0.5M NaOH | 3 | 3 | ≦2.2 |
| CIEX EQ | 50 mM Sodium Acetate, 25 mM NaCl, pH 5.4 | 4 | 3 | |

*Pooling criteria collected 2 CV as product containing CIEX elution pool

Example 16

Optimization of Cation Exchange Product Recovery Via Optimization of the Cation Exchange Low pH Hold and/or Protein A Elution Conditions A clarified IgG containing feed was prepared according to the description in Example 3. The IgG1 was purified from the harvested clarified cell culture fluid (HCCF) using a ProSep Ultra Plus column according to the procedure described in Table 3.1 with the exception of the equilibration buffer being 25 mM Tris, 25 mM NaCl, 0.05M EDTA, pH 7.0. The Protein A elution pool was adjusted to pH 5 and a final concentration of 1.2 g/L. Nine individual 0.5 mL samples of ProRes-S cation exchange resin were measured using disposables column (Evergreen Scientific, Los Angeles Calif.), equilibrated with 5 CV of 50 mM sodium acetate buffer at pH 5 (CIEX EQ Buffer), and added to individual 50 mL plastic centrifuge tubes. The ProRes-S resin samples were loaded to 40 g/L by the addition of 25 mL of the Protein A pool described previously. The protein/resin mixtures were rotated for 4 hrs. The ProRes-S resin samples were then filtered into a disposable chromatography columns and washed with 5 CV of CIEX EQ buffer. The resin samples were subsequently returned to 50 mL centrifuge tubes and a series of 15 mL volumes of low pH wash buffers (as shown in Table 13) were added to mimic the low pH hold step or Protein A elution loading condition for the direct loading of the CIEX from the Protein A column. The 15 mL volume low pH buffers were at pH 3.5 and contained various conductivities due to the addition of sodium chloride described in Table 13. The samples were rotated for 1.5 hours and then transferred to a disposable chromatography column. The samples were then washed with CIEX EQ buffer and eluted with 5 mL of a typical CIEX elution buffer; 200 mM sodium chloride in 50 mM sodium acetate pH 5.4. The product recovery was determined by the absorbance at 280 nm using a extinction coefficient of 1.38. The product recoveries based on the Protein A pool loading are reported in Table 13. Surprisingly, product recovery after exposure to low pH buffers is sensitive to the conductivity of the low pH buffer. The product recovery is greatly improved with the addition of salt in the low pH buffers which would present in the low pH hold and Protein A elution steps.

TABLE 13

Product recovery for various Low pH hold or Protein A elution buffer conductivities

| Protein A pool loading condition | Low pH hold buffer condition | CIEX elution buffer condition | Product Recovery (%) |
|---|---|---|---|
| Sodium Acetate/ Tris pH 5 | Sodium Acetate, pH 3.5 with 0 mM sodium chloride | Sodium Acetate, pH 5.4 with 200 mM NaCl | 19 |
| Sodium Acetate/ Tris pH 5 | Sodium Acetate, pH 3.5 with 25 mM sodium chloride | Sodium Acetate, pH 5.4 with 200 mM NaCl | 59 |
| Sodium Acetate/ Tris pH 5 | Sodium Acetate, pH 3.5 with 50 mM sodium chloride | Sodium Acetate, pH 5.4 with 200 mM NaCl | 79 |
| Sodium Acetate/ Tris pH 5 | Sodium Acetate, pH 3.5 with 75 mM sodium chloride | Sodium Acetate, pH 5.4 with 200 mM NaCl | 87 |
| Sodium Acetate/ Tris pH 5 | Sodium Acetate, pH 3.5 with 100 mM sodium chloride | Sodium Acetate, pH 5.4 with 200 mM NaCl | 90 |
| Sodium Acetate/ Tris pH 5 | Sodium Acetate, pH 3.5 with 125 mM sodium chloride | Sodium Acetate, pH 5.4 with 200 mM NaCl | 90 |
| Sodium Acetate/ Tris pH 5 | Sodium Acetate, pH 3.5 with 150 mM sodium chloride | Sodium Acetate, pH 5.4 with 200 mM NaCl | 92 |
| Sodium Acetate/ Tris pH 5 | Sodium Acetate, pH 3.5 with 175 mM sodium chloride | Sodium Acetate, pH 5.4 with 200 mM NaCl | 85 |
| Sodium Acetate/ Tris pH 5 | Sodium Acetate, pH 3.5 with 200 mM sodium chloride | Sodium Acetate, pH 5.4 with 200 mM NaCl | 86 |

Example 17

Optimization of Cation Exchange Polyclonal IgG Recovery Via Optimization of Protein A Elution Buffer Conductivity (CIEX Loading Buffer) and CIEX A model Protein A elution pool was constructed using the following mixture using 50 mM sodium acetate and 2.5 g/L polyclonal IgG (PAb, SeraCare Life Sciences, Inc., Oceanside, Calif.) at three different pH values; pH 3.5, pH 4 and pH 4.5. Three individual 4.5 mL samples of ProRes-S resin were equilibrated in disposable chromatography column with 50 mM sodium acetate at pH 3.5, pH 4 and pH 4.5 respectively. The resin samples were then added to their respective pH equivalent PAb containing model feed to a load of 40 g/L. Protein binding was allowed to occur overnight while the samples were rotated at 20 rpm. The resin samples were then washed with 10 CV of a pH equivalent equilibration buffer (50 mM acetate, pH 3.5, pH 4 and pH 4.5 respectively).

The samples were then used to form a 10% v/v suspension of bead in a pH equivalent equilibration buffer. The resin was slurried and 10 uL of resin (100 uL of slurry) dispensed into 96 well filter plates (1 um hydrophilic PVDF membrane, Millipore Corp.). The excess low pH buffer from the slurry was removed using a multiwall plate filtration system (Millipore Corporation), thus isolating the 10 uL of ProRes-S resin loaded with PAb. A range of elution buffer conditions (30 individual conditions, 200 uL for each well) were added to the wells in triplicate for each PAb loading pH. The plates were shaken for 1 hour and the absorbance at 280 measured. The absorbance was correlated to the IgG recovery and is reported in Table 14. Surprisingly, the product recovery over a large range of elution conditions is sensitive to the pH under which loading was done.

Though this experiment is a static loading of the resin, the trend is still an important consideration for the optimization of a connected process. The pH of the Protein A elution buffer determines the range of pH conditions the target molecule, such as IgG, will experience during loading of the cation exchange resin during connected processing. Table 14 suggests maintaining the CIEX loading pH value at the highest possible value where protein elution occurs from the affinity column, such as Protein A, should provide the highest product recovery.

TABLE 14

Product recovery for various Protein A elution buffer conductivities

| Buffer Condition | pH | NaCl Concentration (mM) | PAb Recovery for pH 3.5 Loading (%) | PAb Recovery for pH 4 Loading (%) | PAb Recovery for pH 4.5 Loading (%) |
|---|---|---|---|---|---|
| 1 | 6 | 0 | 5 | 5 | 5 |
| 2 | 6.5 | 0 | 5 | 7 | 8 |
| 3 | 7 | 0 | 5 | 14 | 21 |
| 4 | 7.5 | 0 | 5 | 23 | 35 |
| 5 | 8 | 0 | 5 | 27 | 43 |
| 6 | 6 | 50 | 5 | 6 | 7 |
| 7 | 6.5 | 50 | 5 | 16 | 29 |
| 8 | 7 | 50 | 5 | 29 | 52 |
| 9 | 7.5 | 50 | 6 | 44 | 60 |
| 10 | 8 | 50 | 6 | 42 | 66 |
| 11 | 6 | 100 | 5 | 8 | 13 |
| 12 | 6.5 | 100 | 5 | 26 | 40 |
| 13 | 7 | 100 | 5 | 38 | 65 |
| 14 | 7.5 | 100 | 6 | 44 | 72 |
| 15 | 8 | 100 | 6 | 49 | 78 |
| 16 | 6 | 150 | 5 | 14 | 27 |
| 17 | 6.5 | 150 | 5 | 33 | 49 |
| 18 | 7 | 150 | 5 | 44 | 63 |
| 19 | 7.5 | 150 | 6 | 51 | 75 |
| 20 | 8 | 150 | 6 | 54 | 75 |
| 21 | 6 | 200 | 5 | 19 | 37 |
| 22 | 6.5 | 200 | 5 | 31 | 58 |
| 23 | 7 | 200 | 5 | 48 | 71 |
| 24 | 7.5 | 200 | 6 | 52 | 76 |
| 25 | 8 | 200 | 6 | 54 | 83 |
| 26 | 6 | 250 | 5 | 26 | 41 |
| 27 | 6.5 | 250 | 5 | 37 | 62 |
| 28 | 7 | 250 | 5 | 45 | 67 |
| 29 | 7.5 | 250 | 6 | 48 | 83 |
| 30 | 8 | 250 | 6 | 49 | 87 |

Example 18

Characterization of Product Pool Purity

In the Examples set forth herein, the level of IgG aggregate was measured using size exclusion chromatography/HPLC. A Zorbax GF450 (Agilent cat 884973-902, S/N USMX006417) column was operated at a 1 mL/min flow rate using a buffer of 0.2 M sodium phosphate, pH 7. The sample was injected and the retention times compared to known standards.

The level of IgG in solution was alternatively measured using an analytical Protein A column. A Poros A/20 Protein A column (Applied Biosystems) was equilibrated with PBS, eluted with 0.1M Glycine (pH 2.0) and cleaned with 6M guanidine HCl. An IgG standard curve was created using a series of varying injection volumes of polyclonal IgG (Seracare). Samples were injected and IgG concentrations determined from the standard curve.

The elution pool was measure by UV absorbance at 280 nm to determine IgG concentration and yield. The elution pool was also analyzed for CHOP concentration using a commercial enzyme-linked immunosorbent assay (ELISA) kit (All HCP data with CHO HCP ELISA Kit F015, except Table 11, HCP 3G ELISA, F550; Cygnus Technologies Inc., Southport, N.C.). DNA concentrations were determined using a standard pico green assay and Herring sperm DNA as a standard. Protein A concentrations were determined using an ELISA kit (OEM concepts) using n-Protein A as a standard. SDS-PAGE was performed by diluting the samples 2× with 2× Laemmli buffer and then analysis under non-reducing and reducing conditions as appropriate. Gels were loaded with 10 uL of sample per lane and stained with gel code blue (Thermofisher 24592).

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Notwithstanding that the numerical ranges and parameters setting forth the broad scope of the invention are approximations, the numerical values set forth in the specific examples are reported as precisely as possible. Moreover, all ranges taught herein are to be understood to encompass all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of purifying an Fc region containing target protein from one or more impurities in a sample, the method comprising the steps of
    (a) contacting the sample with an affinity chromatography media;
    (b) eluting the Fc region containing target protein from the affinity media;
    (c) contacting the eluate with a cation exchange chromatography media;
    (d) contacting the cation exchange chromatography media with a buffer having a pH lower than 4.0 for a period time suitable for viral inactivation, wherein the buffer conductivity is 5 to 50 mS;
    (e) eluting the Fc region containing target protein from the cation exchange chromatography media;

(f) contacting the eluate with an anion exchange chromatography media; and
(g) recovering the Fc region containing target protein, wherein the method eliminates the need for a holding tank between steps (b) and (c) and steps (e) and (f).

2. A method of purifying an Fc region containing target protein from one or more impurities in a sample, the method comprising the steps of:
(a) contacting the sample with an affinity chromatography media;
(b) eluting the Fc region containing target protein from the affinity media;
(c) contacting the eluate with a cation exchange chromatography media;
(d) contacting the cation exchange chromatography media with a buffer having a pH lower than 4.0 for a period time suitable for viral inactivation, wherein the buffer conductivity is 5 to 50 mS;
(e) eluting the Fc region containing target protein from the cation exchange chromatography media;
(f) contacting the eluate with an anion exchange chromatography media; and
(g) recovering the Fc region containing target protein, wherein the method eliminates the need for a buffer exchange step between steps (b) and (c) and steps (e) and (f).

3. A method of purifying an Fc region containing target protein from one or more impurities in a sample, the method comprising the steps of:
(a) contacting the sample with an affinity chromatography media;
(b) eluting the Fe region containing target protein from the affinity media;
(c) contacting the eluate with a cation exchange chromatography media;
(d) contacting the cation exchange chromatography media with a buffer having a pH lower than 4.0 for a period time suitable for viral inactivation, wherein the buffer conductivity is 5 to 50 mS;
(e) eluting the Fc region containing target protein from the cation exchange chromatography media;
(f) contacting the eluate with an anion exchange chromatography media; and
(g) recovering the Fc region containing target protein, wherein the method eliminates the need for a holding tank and a buffer exchange step between steps (b) and (c) steps (e) and (f).

4. The method of claim 3, wherein the method further comprises a pre-elution step between steps (a) and (b).

5. The method of claim 3, wherein the Fc region containing target protein is selected From the group consisting of an antibody, an immunoadhesion molecule and an Fc fusion protein, and Fc containing fragments thereof.

6. The method of claim 5, wherein the antibody is a monoclonal antibody.

7. The method of claim 3, wherein step (b) comprises the use of a buffer having a pH ranging from 2.0 to 4.0.

8. The method of claim 4, wherein the pre-elution step comprises contacting the affinity media with a cation exchange chromatography buffer.

9. The method of claim 1, wherein the period of time suitable for virus inactivation ranges from 15 through 60 minutes.

10. The method of claim 3, wherein step (e) comprises the use of a buffer having a pH ranging from 5.0 to 9.0.

11. The method of claim 3, wherein step (e) comprises the use of a buffer having a pH ranging from 6.0 to 8.0.

12. The method of claim 3, wherein step (b) comprises the use of a buffer comprising a conductivity ranging from 5 to 50 mS.

13. The method of claim 3, wherein step (b) comprises the use of a buffer comprising a conductivity ranging from 12 to 25 mS.

14. The method of chum 3, wherein the affinity chromatography media comprises protein A or a functional variant thereof.

15. A connected process for purifying an Fc region containing target protein from one or more impurities in a sample, the method comprising the steps of:
(a) contacting the sample with an affinity chromatography media;
(b) eluting the Fc region containing target protein from the affinity media;
(c) contacting the elute with a cation exchange chromatography media;
(d) contacting the cation exchange chromatography media with a buffer having a pH lower than 4.0 for a period time suitable for viral inactivation, wherein the buffer conductivity is 5 to 50 mS;
(e) eluting the Fc region containing target protein from the cation exchange chromatography media;
(f) contacting the eluate with an anion exchange chromatography media and
(g) recovering the Fc region containing target protein.

16. The connected process of claim 15, wherein the process eliminates the need for a holding to and/or a buffer exchange step between steps (b) and (c) and between steps (e) and (f).

* * * * *

UNITED STATES PATENT AND TRADEMARK OFFICE
CERTIFICATE OF CORRECTION

PATENT NO. : 8,536,316 B2                           Page 1 of 1
APPLICATION NO. : 12/851082
DATED : September 17, 2013
INVENTOR(S) : Neil Soice et al.

It is certified that error appears in the above-identified patent and that said Letters Patent is hereby corrected as shown below:

In the Claims:

In column 46, line 63, in claim 1, delete "period time" and insert -- period of time --, therefor.

In column 47, line 16, in claim 2, delete "period time" and insert -- period of time --, therefor.

In column 47, line 32, in claim 3, delete "Fe" and insert -- Fc --, therefor.

In column 47, line 37, in claim 3, delete "period time" and insert -- period of time --, therefor.

In column 47, line 46, in claim 3, delete "(c) steps" and insert -- (c) and steps --, therefor.

In column 48, line 2, in claim 5, delete "From" and insert -- from --, therefor.

In column 48, line 25, in claim 14, delete "chum" and insert -- claim --, therefor.

In column 48, line 35, in claim 15, delete "elute" and insert -- eluate --, therefor.

In column 48, line 38, in claim 15, delete "period time" and insert -- period of time --, therefor.

In column 48, line 47, in claim 16, delete "to" and insert -- tank --, therefor.

Signed and Sealed this
Twenty-third Day of September, 2014

Michelle K. Lee
*Deputy Director of the United States Patent and Trademark Office*